United States Patent
Arai et al.

(10) Patent No.: US 8,064,569 B2
(45) Date of Patent: Nov. 22, 2011

(54) X-RAY CT IMAGING APPARATUS AND IMAGING CONTROL METHOD THEREFOR

(75) Inventors: Yoshinori Arai, Tokyo (JP); Takahiro Yoshimura, Kyoto (JP); Hideki Yoshikawa, Kyoto (JP)

(73) Assignees: Nihon University, Tokyo (JP); J. Morita Manufacturing Corporation, Kyoto (JP)

( * ) Notice: Subject to any disclaimer, the term of this patent is extended or adjusted under 35 U.S.C. 154(b) by 130 days.

(21) Appl. No.: 12/584,150

(22) Filed: Aug. 31, 2009

(65) Prior Publication Data
US 2010/0067650 A1 Mar. 18, 2010

(30) Foreign Application Priority Data

Sep. 1, 2008 (JP) ................................. 2008-223472
Aug. 24, 2009 (JP) ................................ 2009-192945

(51) Int. Cl.
*A61B 6/00* (2006.01)
(52) U.S. Cl. ................................ 378/16; 378/8; 378/108
(58) Field of Classification Search .................. 378/4, 8, 378/16, 19, 38, 98.7, 108, 901
See application file for complete search history.

(56) References Cited

U.S. PATENT DOCUMENTS

| | | | | |
|---|---|---|---|---|
| 6,859,513 B2 * | 2/2005 | Sako | ............................... | 378/16 |
| 7,042,977 B2 * | 5/2006 | Dafni | ............................... | 378/16 |
| 7,277,523 B2 * | 10/2007 | Mattson | .......................... | 378/15 |
| 7,639,779 B2 * | 12/2009 | Kashiwagi et al. | ............. | 378/37 |

FOREIGN PATENT DOCUMENTS

| | | |
|---|---|---|
| JP | H10-225454 A | 8/1998 |
| JP | 2003-245277 A | 9/2003 |

* cited by examiner

*Primary Examiner* — Jurie Yun
(74) *Attorney, Agent, or Firm* — DLA Piper LLP (US)

(57) ABSTRACT

An X-ray CT imaging apparatus includes an X-ray generating section, an X-ray image capturing section, a supporting section, a holding section, a rotation driving section, and an X-ray controlling section, wherein the X-ray generating section generates an X-ray cone beam, the X-ray image capturing section detects the X-ray cone beam having passed through an object, the supporting section supports the X-ray generating section and the X-ray image capturing section with the object positioned therebetween, the holding section holds the object, the rotation driving section rotates the supporting section relatively to the object, and the X-ray controlling section alleviates an influence of a high X-ray absorption region, present inside the object, in the X-ray image capturing section by means of a control model formed based upon information on the high X-ray absorption region.

21 Claims, 21 Drawing Sheets

F I G. 3
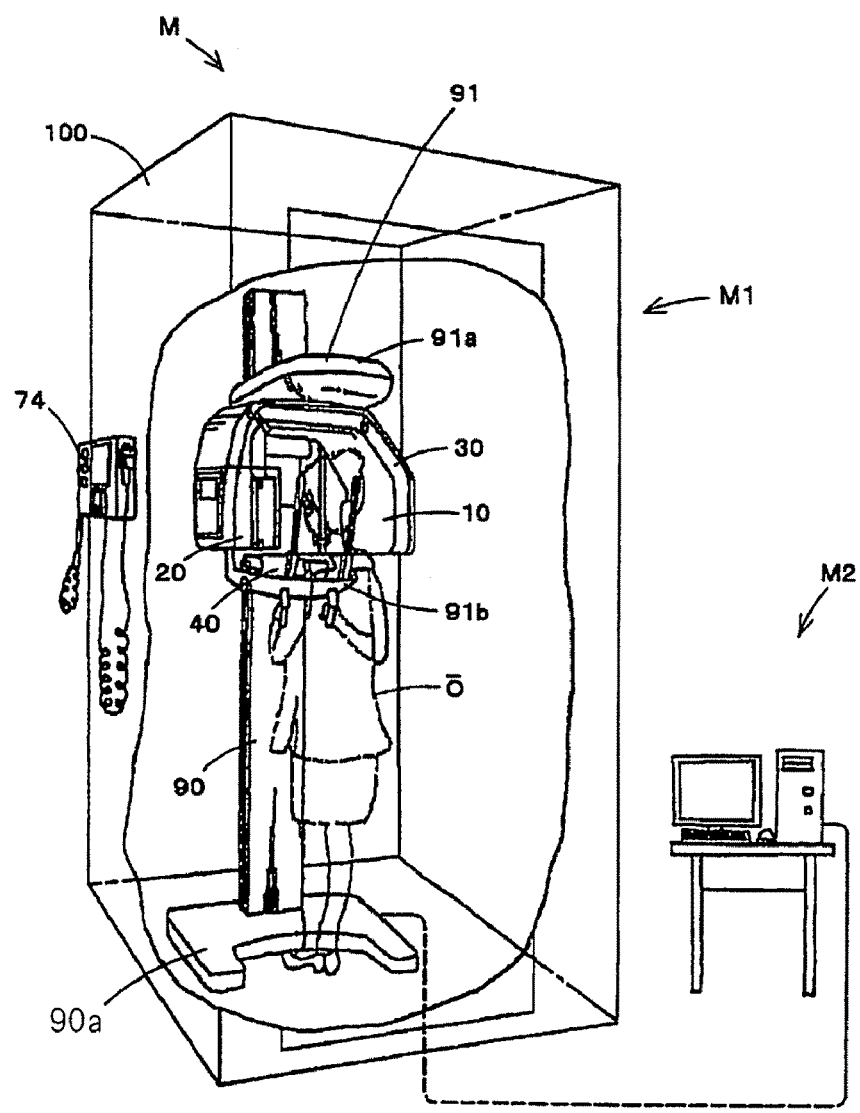

F I G. 7
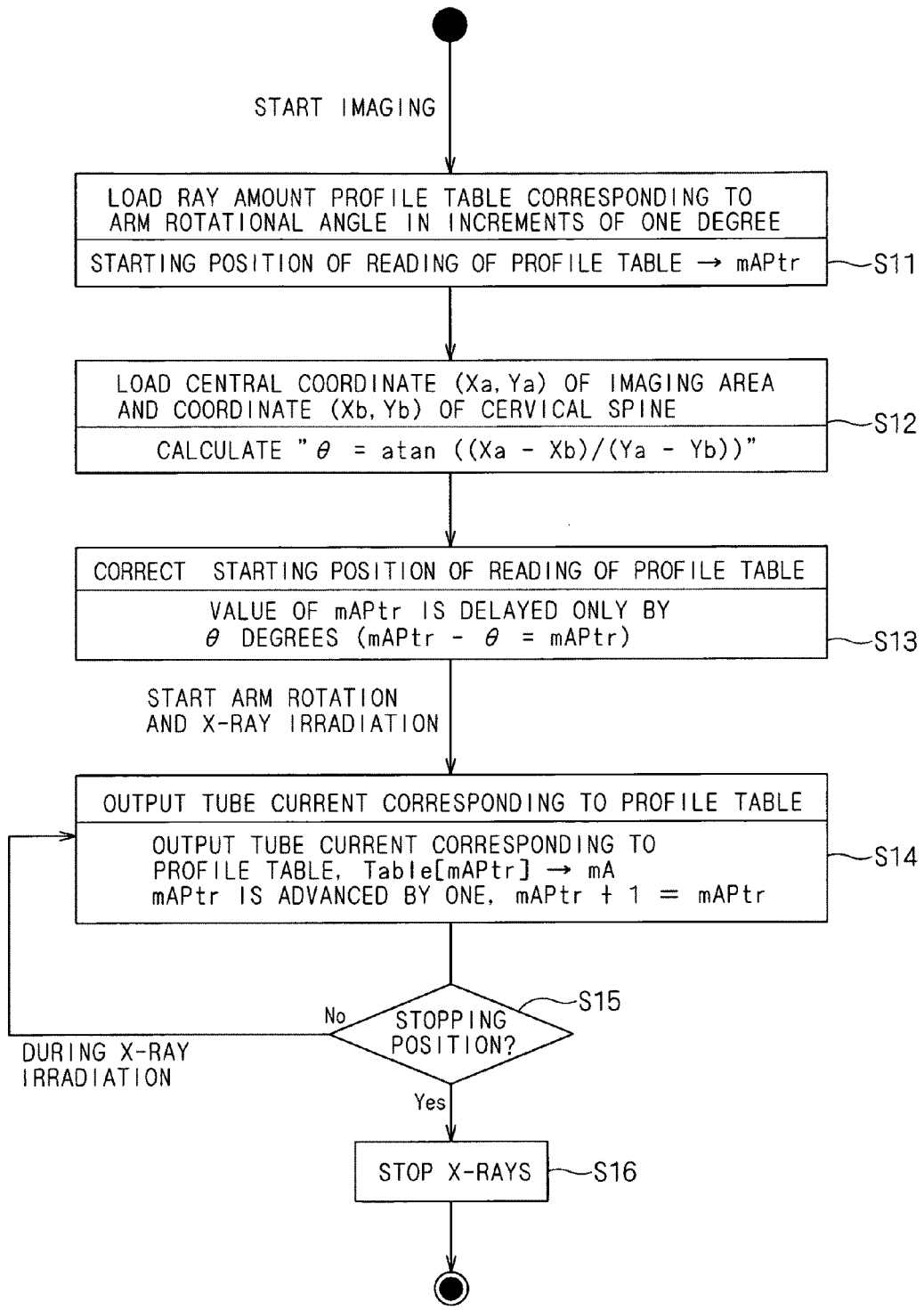

FIG. 14
(a) 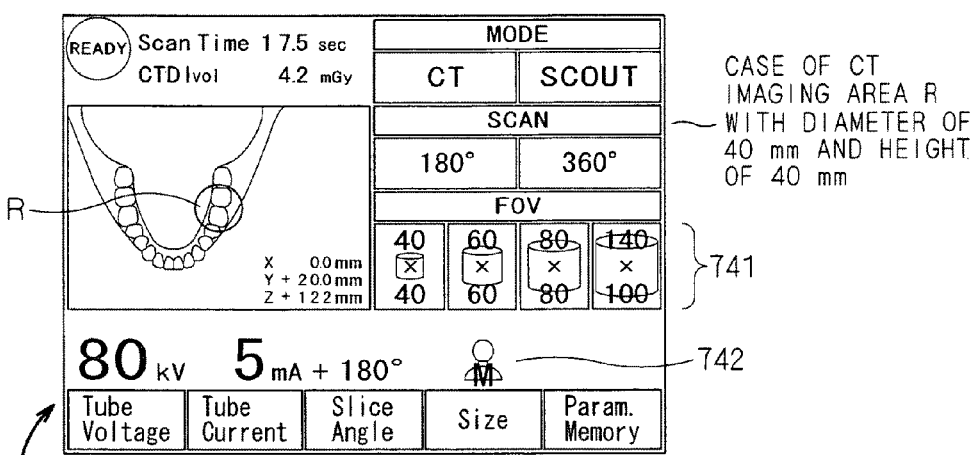
CASE OF CT IMAGING AREA R WITH DIAMETER OF 40 mm AND HEIGHT OF 40 mm
(b) 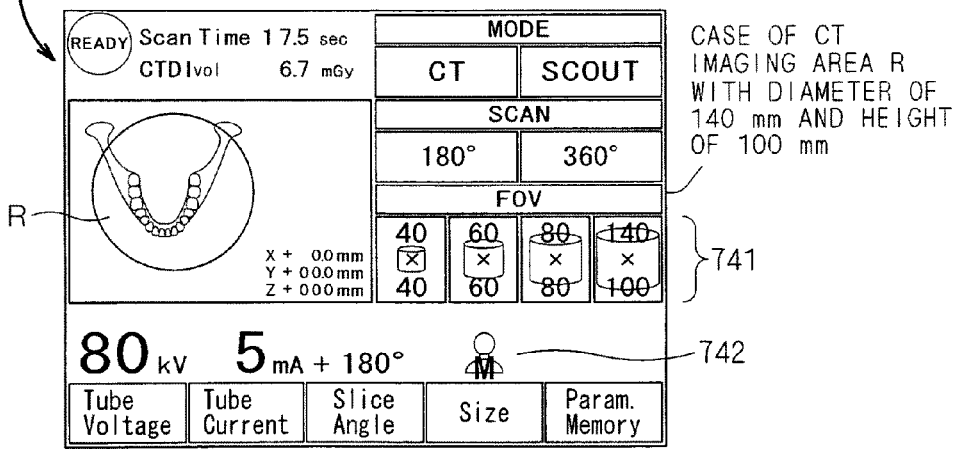
CASE OF CT IMAGING AREA R WITH DIAMETER OF 140 mm AND HEIGHT OF 100 mm

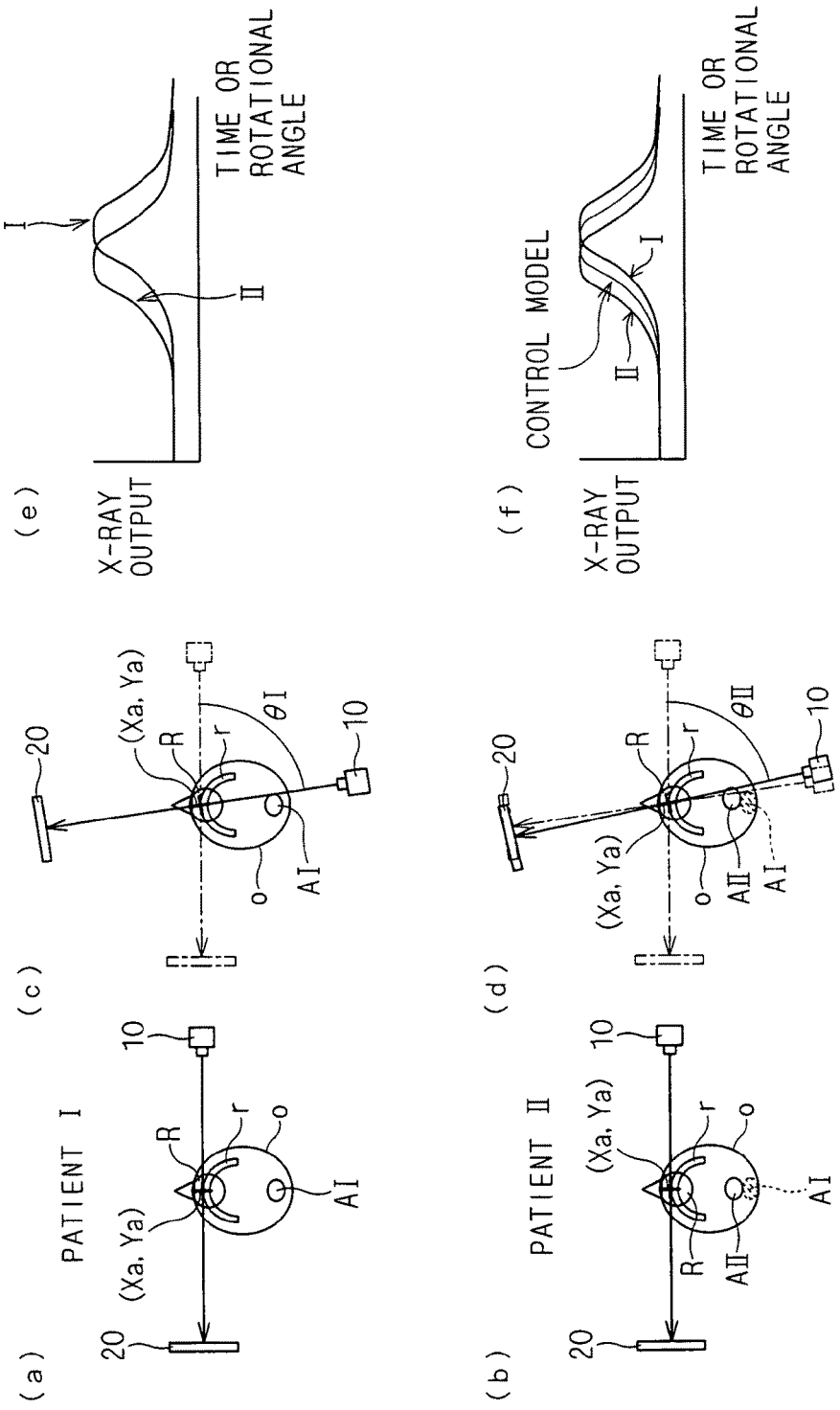

X-RAY CT IMAGING APPARATUS AND IMAGING CONTROL METHOD THEREFOR

BACKGROUND OF THE INVENTION

1. Field of the Invention

The present invention relates to an X-ray CT imaging apparatus and an imaging control method therefor, and particularly relates to an X-ray CT imaging apparatus and an imaging control method therefor, which are capable of alleviating an influence of a high X-ray absorption region that is present inside an object and has an influence on an imaging result.

2. Description of the Background Art

In the field of X-ray diagnosis for medical use, an X-ray CT (computerized tomography) imaging apparatus for tomographically imaging an arbitrary region of a human body is widely known. In this X-ray CT imaging apparatus, an X-ray generating section and an X-ray imaging means being opposed thereto are rotated 360 degrees around an object, and obtained image information is subjected to computer processing, to obtain an CT image of an arbitrary region of a head, a body or the like having been cut off.

Especially in the field of dental treatment, at the time of an implant operation or the like, grasping a thickness, a structure and the like of a cervical spine beforehand facilitates the operation, and hence a small-sized X-ray CT imaging apparatus capable of performing X-ray CT imaging of a specific tooth and its vicinity has been considered.

In this small-sized X-ray CT imaging apparatus, a supporting means supports the X-ray generating section and the X-ray image capturing means in a mutually opposed manner with an object positioned therebetween, and is rotated 360 degrees around the object, to obtain image information. The obtained image information is stored in a storage means, and the stored image information is subjected to image processing such as reconstruction by a computer, to obtain a desired CT image.

Specifically, the X-ray CT imaging apparatus for use in the dental field is described in Japanese Patent Application Laid-Open No. H10-225454 and Japanese Patent Application Laid-Open No. 2003-245277.

SUMMARY OF THE INVENTION

In the X-ray CT imaging apparatus, when a large bone structure or the like is reflected in a plurality of pieces of X-ray imaged image information at the time of CT image processing, a large amount of X-rays is absorbed in that portion, thereby making it difficult to obtain a clear CT image. Namely, the large bone structure or the like is a region that has an influence on an imaging result, and referred to as a high X-ray absorption region in the present specification. For example, in the case of the field of dental treatment, a human head is CT imaged normally with an angle of not smaller than 180 degrees, preferably with 360 degrees, but at this time, an X-ray cone beam from the X-ray generating section passes through a cervical spine as the high X-ray absorption region in a specific range to reach the X-ray imaging means, and hence an amount of X-rays that reach the X-ray imaging means is significantly different from the other ranges. Namely, image information obtained in the specific range becomes a relatively dark image as compared with image information obtained in the other ranges.

For this reason, in the X-ray CT imaging apparatus described in Japanese Patent Application Laid-Open No. H10-225454, a gain adjustment circuit is controlled based upon a detection image density in the X-ray image capturing means. Further, in the X-ray CT imaging apparatus described in Japanese Patent Application Laid-Open No. H10-225454, when the adjustment in the gain adjustment circuit is insufficient, a tube current of an X-ray source or a rotational speed of the supporting means is adjusted so as to adjust an image density.

However, in the X-ray CT imaging apparatus described in Japanese Patent Application Laid-Open No. H10-225454, the need for providing the gain adjustment circuit in the X-ray imaging means causes problems of making the apparatus itself complex and cost high. Further, since the technique described in Japanese Patent Application Laid-Open No. H10-225454 is control in accordance with the amount of transmitted X-rays having transmitted through the object, for example in the case of performing CT imaging of a head where the teeth have a denture made of metal or the like and that portion is constantly included in an irradiation field, the X-rays are absorbed into the denture, leading to constant supply of an excess amount of X-rays regardless of the cervical spine, and there has thus been a possibility that image data required for reconstruction cannot be obtained.

Accordingly, an object of the present invention is to provide an X-ray CT imaging apparatus and an imaging control method therefor, which are capable of alleviating an influence of a high X-ray absorption region as a region, being present inside an object and having an influence on an imaging result, with a simple configuration at low cost, to perform CT imaging with an appropriate X-ray amount even with a denture or the like present in a region of an object to be imaged.

In order to solve the above problems, an X-ray CT imaging apparatus according to a first aspect includes: an X-ray generating section for generating an X-ray cone beam; an X-ray image capturing section for detecting the X-ray cone beam having passed through an object; a supporting section for supporting the X-ray generating section and the X-ray image capturing section with the object positioned therebetween; a holding section for holding the object; a rotation driving section for rotating the supporting section relatively to the object; and an X-ray controlling section for alleviating an influence of a high X-ray absorption region, present inside the object, in the X-ray image capturing section by means of a control model formed based upon high X-ray absorption region information as information on a position of the high X-ray absorption region.

It is thereby possible to alleviate an influence of a high X-ray absorption region as a region, being present inside an object and having the influence on an imaging result, with a simple configuration at low cost, to perform CT imaging. Further, even if CT imaging is performed such that the teeth have a denture made of metal or the like and its portion is constantly included in an irradiation field in CT imaging of a head, control is consistently made in accordance with a control model, and it is thereby possible to perform CT imaging with an appropriate X-ray amount.

Further, an X-ray CT imaging apparatus according to a second aspect further includes a region information acquiring section for acquiring the high X-ray absorption region information, and the X-ray controlling section alleviates the influence of the high X-ray absorption region in the X-ray image capturing section by means of the control model formed based upon the high X-ray absorption region information acquired in the region information acquiring section.

It is thereby possible alleviate the influence of the high X-ray absorption region, present inside the object, with a simple configuration at low cost, to perform CT imaging.

Further, an X-ray CT imaging apparatus according to a third aspect further includes: a central axis setting section for setting a position of a rotation central axis of the X-ray generating section and the X-ray image capturing section; and a rotation central axis shifting section for shifting the position of the rotation central axis relatively to the object in a two-dimensional direction crossing a direction of the rotation central axis based upon the setting in the central axis setting section, and the X-ray controlling section alleviates the influence of the high X-ray absorption region in the X-ray image capturing section by means of the control model formed in consideration of the position of the rotation central axis.

It is thereby possible to perform CT imaging having a degree of freedom at a rotation central axis.

An X-ray CT imaging apparatus according to a fourth aspect further includes an X-ray transmission amount monitoring section for monitoring an amount of transmitted X-rays in a place constantly irradiated with the X-ray cone beam, and the X-ray transmission amount monitoring section corrects the control model of the X-ray controlling section so as to make the monitored amount of transmitted X-rays a substantially constant value.

It is thereby possible to further alleviate the influence of the high X-ray absorption region, to perform CT imaging.

In an X-ray CT imaging apparatus according to a fifth aspect, the X-ray controlling section controls at least one of an output of the X-ray cone beam and a relative rotational speed of the supporting section by means of the control model in accordance with a rotational angle of the supporting section.

It is thereby possible to alleviate the influence of the high X-ray absorption region with ease at low cost through use of an X-ray generating section controlling section, a rotation driving mechanism of a supporting section such as a rotational arm, or the like which is provided in the X-ray CT imaging apparatus, to perform CT imaging.

In an X-ray CT imaging apparatus according to a sixth aspect, the X-ray controlling section changes at least one of a tube current and a tube voltage of the X-ray generating section, to control the output of the X-ray cone beam.

It is thereby possible to alleviate the influence of the high X-ray absorption region with ease at low cost through use of the X-ray generating section controlling section or the like which is provided in the X-ray CT imaging apparatus, to perform CT imaging.

In an X-ray CT imaging apparatus according to a seventh aspect, the X-ray controlling section changes a rotational speed of at least one of the supporting section and the object by the rotation driving section, to control the relative rotational speed of the supporting section.

It is thereby possible to alleviate the influence of the high X-ray absorption region with ease at low cost through use of the rotation driving mechanism of the supporting section such as the rotational arm, or the like which is provided in the X-ray CT imaging apparatus, to perform CT imaging.

In an X-ray CT imaging apparatus according to an eighth aspect, the region information acquiring section acquires high X-ray absorption region information from a scout image obtained by scout-imaging of the object before X-ray CT imaging.

Thereby, since the region information acquiring section acquires the high X-ray absorption region information from a scout image obtained by scout imaging the object before X-ray CT imaging, it is possible to specify and acquire the high X-ray absorption region with ease and accuracy.

In an X-ray CT imaging apparatus according to a ninth aspect, the scout image is at least one of an image obtained by imaging the object from two different directions and a curved surface tomographic image of the object.

It is thereby possible to specify and acquire the high X-ray absorption region with ease and accuracy.

In an X-ray CT imaging apparatus according to a tenth aspect, the scout image is an image read from a storage section inside the X-ray CT imaging apparatus or an external storage section, associated hereto.

Thereby, auxiliary imaging becomes unnecessary to simplify CT imaging, and also in the case of the auxiliary imaging being X-ray imaging, a dose given to the object can be reduced.

In an X-ray CT imaging apparatus according to an eleventh aspect, the region information acquiring section specifies the high X-ray absorption region from the scout image by image pattern recognition.

It is thereby possible to alleviate an operational load of an operator.

In an X-ray CT imaging apparatus according to a twelfth aspect, the region information acquiring section selects a body type of the object from predetermined alternatives, to acquire the high X-ray absorption region information previously set in accordance with the predetermined alternative.

Thereby, the operation to specify a position of an individual object of the region becomes unnecessary, and auxiliary imaging also becomes unnecessary.

In an X-ray CT imaging apparatus according to a thirteenth aspect, the region information acquiring section specifies the high X-ray absorption region based upon measurement data of the object.

Thereby, auxiliary imaging becomes unnecessary to simplify CT imaging, and also in the case of the auxiliary imaging being X-ray imaging, a dose given to the object can be reduced.

In an X-ray CT imaging apparatus according to a fourteenth aspect, measurement of the object is performed by use of the holding section.

Thereby, there is no need for preparing another measurement instrument for specifying the high X-ray absorption region.

In an X-ray CT imaging apparatus according to a fifteenth aspect, the high X-ray absorption region is a cervical spine.

It is thereby possible to alleviate an influence on an imaging result of a cervical spine, to perform CT imaging.

In an X-ray CT imaging apparatus according to a sixteenth aspect, an object to be imaged of the X-ray CT imaging apparatus is only a local portion of the object.

It is thereby possible to perform CT imaging of only a necessary portion, to reduce the dose of the object.

In an X-ray CT imaging apparatus according to a seventeenth aspect, each of the control models that are different is set with respect to each of the local portions of the object.

It is thereby possible to alleviate the influence of the high X-ray absorption region, to perform CT imaging.

Further, an imaging control method for an X-ray CT imaging apparatus according to an eighteenth aspect includes the steps of: (a) holding an object in an holding section; (b) making an X-ray image capturing section detect an X-ray cone beam from an X-ray generating section, having passed through the object, while rotating a supporting section for supporting the X-ray generating section and the X-ray image capturing section relatively to the object; and (c) making an X-ray controlling section alleviate an influence of a high X-ray absorption region, present inside the object held in the step (a), in the X-ray image capturing section during processing of the step (b) by means of a control model formed based upon high X-ray absorption region information as information concerning a position of the high X-ray absorption region.

It is thereby possible to alleviate an influence of a high X-ray absorption region, present inside an object, with a simple configuration at low cost, to perform CT imaging.

Further, an imaging control method for an X-ray CT imaging apparatus according to a nineteenth aspect further includes the steps of: (d) acquiring the high X-ray absorption region information by use of a region information acquiring section; and (e) selecting a control model formed based upon the high X-ray absorption region information acquired in the step (d), to make the X-ray controlling section alleviate the influence of the high X-ray absorption region in the X-ray image capturing section.

It is thereby possible to alleviate an influence of a high X-ray absorption region, present inside an object, with a simple configuration at low cost, to perform CT imaging.

Further, an imaging control method for an X-ray CT imaging apparatus according to a twentieth aspect further includes the steps of: (f) setting a position of a rotation central axis of the X-ray generating section and the X-ray image capturing section by use of a central axis setting section after the step (a); and (g) making a rotation central axis shifting section shift the position of the rotation central axis relatively to the object in two-dimensional directions crossing a direction of the rotation central axis, based upon the setting in the step (f), and the X-ray controlling section alleviates the influence of the high X-ray absorption region in the X-ray image capturing section by means of the control model formed in consideration of the position of the rotation central axis in the setting of the step (f).

It is thereby possible to perform CT imaging having a degree of freedom at a rotation central axis.

Further, in an imaging control method for an X-ray CT imaging apparatus according to a twenty-first aspect, the X-ray controlling section controls at least one of an output of the X-ray cone beam and a relative rotational speed of the supporting section during processing of the step (b) by means of the control model, to alleviate the influence of the high X-ray absorption region in the X-ray image capturing section while keeping an appropriate X-ray amount.

It is thereby possible to alleviate the influence of the high X-ray absorption region with ease at low cost through use of an X-ray generating section controlling section, a rotation driving mechanism of a supporting section such as a rotational arm, or the like which is provided in the X-ray CT imaging apparatus, to perform CT imaging.

These and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a schematic view of the X-ray CT imaging apparatus according to Embodiment 1;

FIG. 7 is a flowchart explaining an operation of the X-ray CT imaging apparatus according to Embodiment 1;

FIG. 14 is a view for explaining the operation of the X-ray CT imaging apparatus according to Embodiment 3;

FIGS. 19 to 23 are views each for explaining an operation of an X-ray CT imaging apparatus according to Embodiment 5.

DESCRIPTION OF THE PREFERRED EMBODIMENTS

Embodiment 1

In the following described is an example of an X-ray imaging apparatus (X-ray CT imaging apparatus) that is used in the dental field and performs CT imaging of a maxillofacial area of an object.

Figure 1:
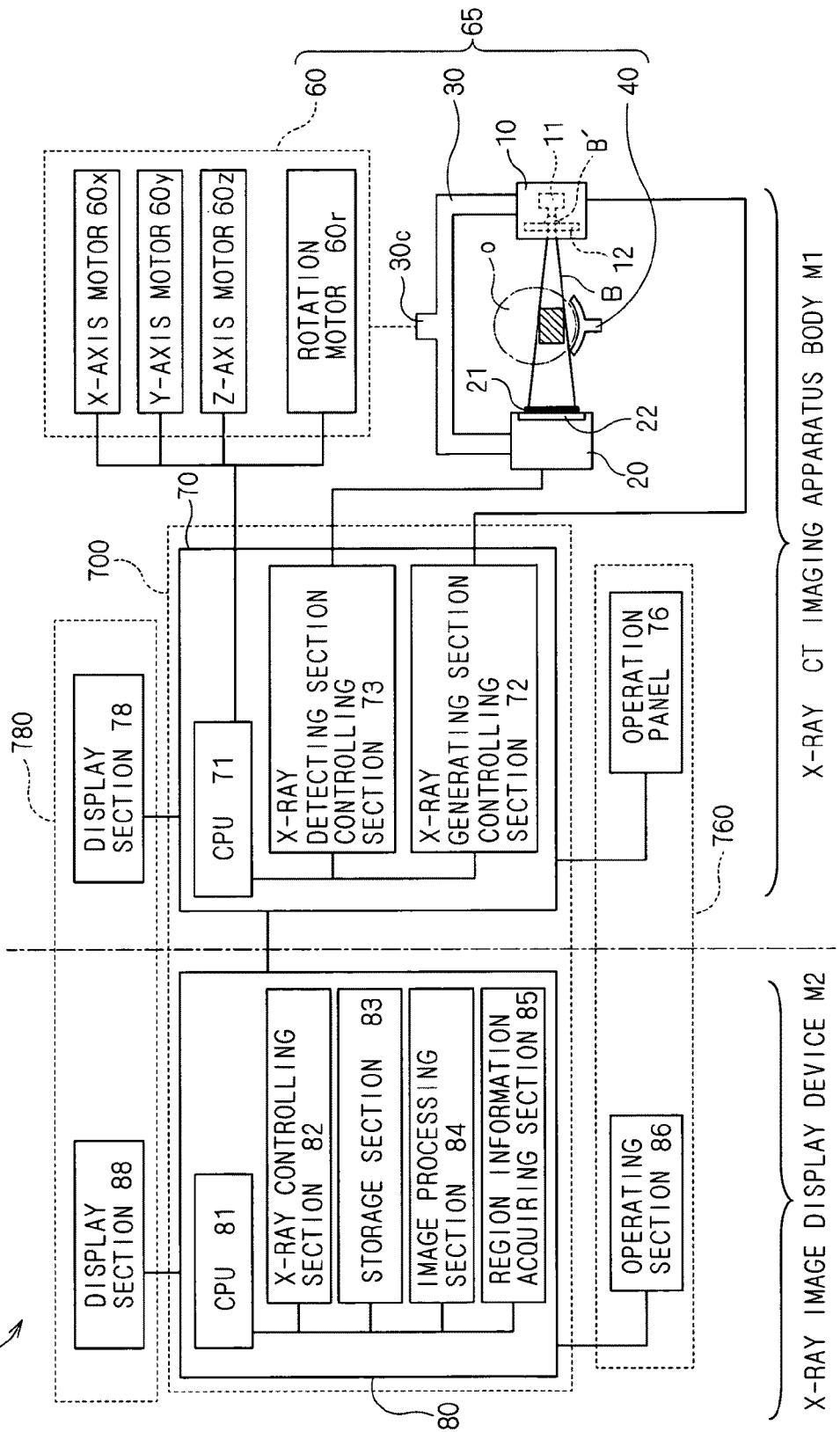
FIG. 1 is a block diagram of an X-ray CT imaging apparatus according to Embodiment 1.

FIG. 1 is a block diagram explaining a basic configuration of an X-ray CT imaging apparatus M. The X-ray CT imaging apparatus M includes an X-ray CT imaging apparatus body M1 and an X-ray image display device M2, and has a configuration of these transmitting and receiving data through a communication cable or the like.

The X-ray CT imaging apparatus body M1 includes: a supporting section 30 that supports an X-ray generating section 10 and an X-ray image capturing section 20 in a mutually opposed manner; a driving section 60 that drives the supporting section 30; and an imaging apparatus controlling section 70, and the imaging apparatus controlling section 70 is added with an operation panel 76. This operation panel 76 is used for the purpose of setting the X-ray generating section 10 and the X-ray image capturing section 20, or specifying a later-mentioned high X-ray absorption region as a region to have an influence on an imaging result, or for some other purpose. An object o is held in a holding section 40 such as a chin rest and a chair.

The X-ray generating section 10 is configured of an X-ray generator 11 that has an X-ray tube for irradiation of X-rays and the like, and an irradiation field controlling section 12 that has a slit or the like which controls expansion of X-ray cone beam B' to give an X-ray cone beam B, and the X-ray image capturing section 20 is configured of a cassette 22 provided with an X-ray detector 21 having a two-dimensionally expanded CCD sensor or the like. Although the cassette 22 is insertable into and removable from the X-ray image capturing section 20, the X-ray detector 21 may be provided fixedly to the X-ray image capturing section 20 without the cassette 22. The driving section 60 includes an X-axis motor 60x and a Y-axis motor 60y that collaborate with each other to horizontally shift a rotation central axis 30c of the supporting section 30, a Z-axis motor 60z for elevating the supporting section 30, and a rotation motor 60r for rotating the supporting section 30 around the rotation central axis 30c.

It is to be noted that the rotation motor 60r may be made to rotate the rotation central axis 30c portion that is fixed to the supporting section 30, or in a structure where the supporting section 30 is rotatable with respect to the rotation central axis 30c, the rotation motor 60r may be provided inside the supporting section 30 to rotate the supporting section 30 with respect to the rotation central axis 30c portion. Similarly, the X-axis motor 60x and the Y-axis motor 60y are made to horizontally shift the rotation central axis 30c portion of the supporting section 30, or in a structure where the supporting section 30 is horizontally displaceable with respect to the rotation central axis 30c portion, the X-axis motor 60x and the Y-axis motor 60y are provided inside the supporting section 30 so as to horizontally shift the supporting section 30 with respect to the rotation central axis 30c portion.

The rotation motor 60r, the X-axis motor 60x, the Y-axis motor 60y and the Z-axis motor 60z constitute a driving section 60 to serve as a driving source for shifting the supporting section 30 relatively to the object o. It should be noted that the supporting section 30, the holding section 40 and the driving section 60 correspond to a shifting section 65 for shifting the X-ray generating section 10 and the X-ray image capturing section 20 relatively to the object o.

The imaging apparatus controlling section 70 includes: a CPU 71 that executes a variety of control programs including a control program for controlling the driving section 60; an X-ray generating section controlling section 72 that controls the X-ray generating section 10; and an X-ray image capturing section controlling section 73 that controls the X-ray image capturing section 20. It is to be noted that the variety of control programs are stored in a storage section, and the CPU 71 reads the variety of control programs from the storage section and executes the programs. As the storage section, in fact, a variety of a ROM and a RAM can be used, and an EEPROM and a flash ROM are also usable. In FIG. 1, the X-ray image generating section controlling section 72 is indicated as an X-ray generating section controlling section 72, and also the X-ray image capturing section controlling section 73 is indicated as an X-ray detecting section controlling section 73. The image display device controlling section 80 includes a CPU 81 that executes a control program for controlling the X-ray CT imaging apparatus body M1, a processing program for processing data on an image taken, and some other program. It should be noted that the processing program is stored in the storage section such as the flash ROM or the like, and the CPU 81 reads the processing program from the storage section and executes the program. Further, the image display device controlling section 80 includes: an X-ray controlling section 82 that controls the X-ray generating section controlling section 72 and the X-ray image capturing section controlling section 73 in accordance with a control model; a storage section 83 that stores image data and the like; an image processing section 84 that carries out predetermined processing on an image taken; and a region information acquiring section 85 that acquires information on a high X-ray absorption region present inside the object.

The operation panel 76 is configured of a small-sized liquid crystal panel and a plurality of operation buttons. As input sections of the operation panel 76, other than the operation buttons, input sections such as a keyboard, a mouse and a touch pen are also usable.

The display section 78 displays information such as a character and an image which are required for an operation of the X-ray CT imaging apparatus body M1. Further, the display section 78 may be connected with the later-mentioned X-ray image display device M2, to display contents of display that are displayed in the display section 88 of the X-ray image display device M2. Moreover, the display section 78 may be a display such as a liquid crystal monitor and configured integrally with the operation panel 76. Furthermore, a character and an image displayed in the display section 88 may be pointer-operated by use of the mouse or the like of the operation section 86, to form a configuration where a variety of commands can be issued to the X-ray CT imaging apparatus body M1.

Since the X-ray CT imaging apparatus M shown in FIG. 1 is configured to be separated into the X-ray CT imaging apparatus body M1 and the X-ray image display device M2, it is configured so as to be of the imaging apparatus controlling section 70 and the image display device controlling section 80; the operation panel 76 and the operation section 86; and the display section 78 and the display section 88. However, the X-ray CT imaging apparatus M shown in FIG. 1 may be regarded as being configured of a control section 700 made up of the imaging apparatus controlling section 70 and the image display device controlling section 80; an operation section 760 made up of the operation panel 76 and the operating section 86; and a display section 780 made up of the display section 78 and the display section 88. The display section 780 may, for example, be configured of a liquid crystal display touch panel, to also serve as the operation section 760.

The X-ray CT imaging apparatus body M1 executes panorama imaging of the object and CT imaging of the object in accordance with a command from the operation panel 76 or the X-ray image display device M2. Further, the X-ray CT imaging apparatus body M1 receives a variety of commands, coordinate data and the like from the X-ray image display device M2, and also transmits data on an image taken to the X-ray image display device M2.

Figure 2:
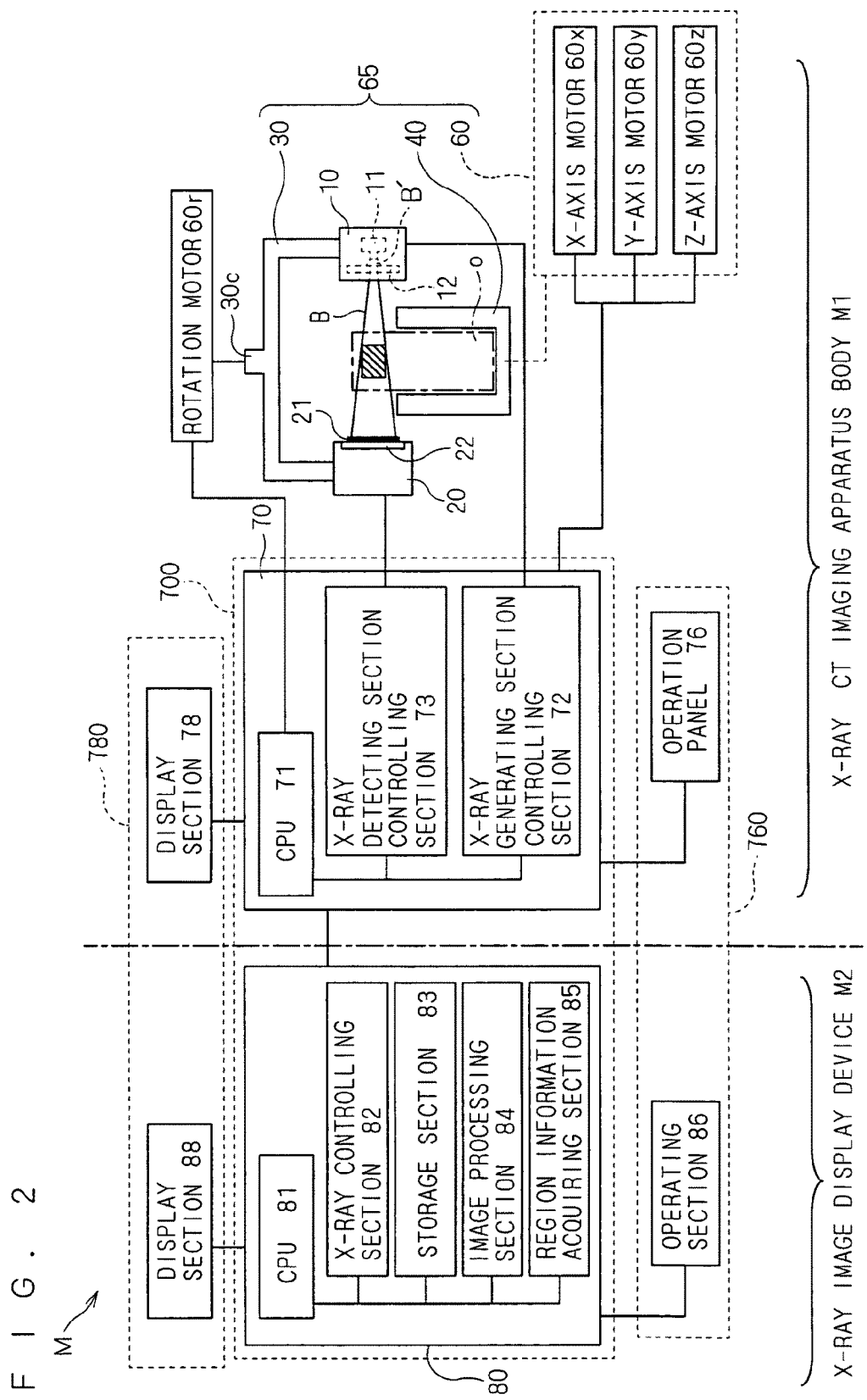
FIG. 2 is a block diagram of another X-ray CT imaging apparatus according to Embodiment 1.

FIG. 2 is a block diagram explaining the X-ray CT imaging apparatus M different from the X-ray CT imaging apparatus M shown in FIG. 1. A basic configuration is the same as that of the X-ray CT imaging apparatus M shown in FIG. 1. However, although the X-ray CT imaging apparatus body M1 shown in FIG. 2 is common in that the rotation motor 60r for rotating the supporting section 30 is provided, it is different in that the X-axis motor 60x and the Y-axis motor 60y for shifting the rotation central axis 30c portion of the supporting section 30 and the Z-axis motor 60z for elevating the supporting section 30 are not provided, and the X-axis motor 60x and the Y-axis motor 60y which collaborate with each other to horizontally shift the holding section 40 for holding the object o and the Z-axis motor 60z for elevating the holding section 40 are provided.

As described above, a variety of mechanisms to shift the supporting section 30 relatively to the object o can be considered. The configuration may be formed such that part of each of the X-axis motor 60x, the Y-axis motor 60y and the Z-axis motor 60z are provided on the driving side of the supporting section 30 and the remaining parts thereof are provided on the driving side of the holding section 40, and further, at least part of each of the X-axis motor 60x, the Y-axis motor 60y and the Z-axis motor 60z are provided on each driving side.

FIG. 3 is a schematic view more specifically showing the X-ray CT imaging apparatus M. The X-ray CT imaging apparatus body M1 shown in FIG. 3 includes the supporting section 30 that is configured as a rotational arm with the rotation motor 60r built therein and supports at its both ends the X-ray generating section 10 and the X-ray image capturing section 20 in a mutually opposed manner, as does the X-ray CT imaging apparatus body M1 shown in FIGS. 1 and 2. This apparatus has a basic configuration closer to that of the X-ray CT imaging apparatus M shown in FIG. 1, but has a structure where, as for elevating shift, the holding section 40 is fixed to a later-mentioned elevating frame 91 for suspending the supporting section 30, and hence, when the supporting section 30 is elevated, the holding section 40 is also elevated with the elevation of the supporting section 30. Therefore, the supporting section 30 is elevated in concert with a height of the object o, so that the object o can be introduced to the holding section 40 in an appropriate position.

With respect to a pillar 90 elected on a base 90a, the elevating frame 91 having a substantially U shape with an upper frame 91a and a lower frame 91b protruding forward is provided in an elevatable manner by an elevating mechanism, not shown. The supporting section 30 is suspended from the elevating frame 91, and as in the X-ray CT imaging apparatus body M1 shown in FIGS. 1 and 2, the X-axis motor 60x and the Y-axis motor 60y for horizontally shifting a rotational axis of the supporting section 30 are built in the elevating frame 91.

The X-ray generating section 10, the X-ray image capturing section 20, the supporting section 30, the elevating frame 91 and the like of the X-ray CT imaging apparatus body M1 are provided inside a box 100 as an X-ray-proof room that shields X-rays. Further, an operation panel 74 is provided on the side surface of the box 100. Moreover, in the X-ray CT imaging apparatus M shown in FIG. 3, the X-ray CT imaging apparatus body M1 and the X-ray image display device M2 are connected through a wired cable.

Next, an operation of the X-ray CT imaging apparatus according to the present embodiment is described by use of the X-ray CT imaging apparatus M shown in FIGS. 1 to 3. In the X-ray CT imaging apparatus according to the present embodiment, at the time of performing CT imaging of the object, the X-ray CT imaging apparatus M is controlled so as to alleviate an influence of a high X-ray absorption region (e.g. cervical spine), which is a region being present inside the object and having the influence on an imaging result, on an image acquired in the X-ray image capturing section 20 by means of a control model based upon information on the region. Information on a position of the high X-ray absorption region is the high X-ray absorption region information. In a flowchart shown in FIG. 4, before CT imaging is performed so that the region information acquiring section 85 acquires the high X-ray absorption region information, bidirectional X-ray scout imaging is performed (Step S1). The bidirectional X-ray scout imaging has a configuration where transmitted images of the object are taken with a plurality of different angles, to be used as scout images, and a configuration as in Japanese Patent Application Laid-Open No. 2004-329293 applied by the present applicant. It is to be noted that in the present embodiment, the X-ray CT imaging apparatus M where information on the region is acquired by the region information acquiring section 85 is described, but the present invention is not limited thereto, and the apparatus may be configured such that a high X-ray absorption region is decided based upon average bone information, and a control model based thereupon is fixed to one. This configuration may be formed because the high X-ray absorption region is located in almost the same position when the object is a human, and hence, if an individual difference is ignored the influence of the region on an acquired image can almost be alleviated. In this case, provision of the region information acquiring section 85 is not required, but only preparation of a control model based upon high X-ray absorption region information is required. Here, having an influence on the imaging result means coming into a state where, for example speaking of the cervical spine, X-rays pass through not only the teeth but also the cervical spine in the case of performing CT imaging of the teeth, and thereby the X-rays that reach or pass through the teeth are attenuated to make it difficult to obtain a clear CT image, the state including the case of X-ray transmission data required for reconstruction of the teeth being insufficient in terms of a density or a CT value.

When the influence of the region is wished to be more accurately alleviated, a configuration described below may be adopted. In the flowchart shown in FIG. 4, a bidirectional X-ray scout image is taken by use of the X-ray generating section 10, the X-ray image capturing section 20, and the like. FIG. 5 shows an X-ray scout image P1 having an X-ray transmitted image P11 obtained by imaging a maxillofacial area of the object o from the front surface and an X-ray transmitted image P12 obtained by imaging the maxillofacial area from the side surface. In Step S2 shown in FIG. 4, the X-ray scout image P1 shown in FIG. 5 is displayed in the display section 780. It should be noted that FIG. 5 shows a cursor he indicating a horizontal position and a cursor vc indicating a vertical position.

Next, with the high X-ray absorption region that is present inside the object regarded as the cervical spine in this case, a cervical spine acquirement mode for acquiring positional information on the cervical spine from the X-ray scout image P1 is selected, and the process advances to Step S3. In Step S3, using the operation section 760, a cervical spine A is designated from the X-ray scout image P1 displayed in the operation panel 780. As a method for the designation, in Step S 4, the center of the cervical spine is selected by use of the designation section 760 such as the mouse. It is to be noted that the present invention is not limited to the above method, and for example, a method for designating four corners of the cervical spine A displayed in the X-ray scout image P1 shown in FIG. 5 may be employed. From the position of the cervical spine A on the X-ray scout image P1 selected in Step S 3, the region information acquiring section 85 recognizes a two-dimensional coordinate (Xb, Yb) of the cervical spine (Step S4).

Next, for the purpose of designating an area where CT imaging is performed by use of the X-ray scout image P1, a scout positioning mode is selected. In the scout positioning mode, the center of the CT imaging area in the X-ray scout image P1 is selected (Step S5). Specifically, the cursors hc, vc shown in FIG. 5 are shifted by use of the mouse or the like, to select the center of the CT imaging area. From the position of the center of the CT imaging area on the X-ray scout image P1 selected in Step S5, the CPU 81 or the like recognizes a two-dimensional coordinate (Xa, Ya) of the center of the CT imaging area (Step S6). In addition, the rotation central axis of the X-ray generating section 10 and the X-ray image capturing section 20 as the center of the CT imaging area is set by a central axis setting section that is realized by the CPU 81.

Next, in Step S7, CT imaging is performed with the coordinate (Xa, Ya) regarded as the center, and at that time, the X-ray controlling section 82 changes an output of the X-ray generating section 10, a rotational speed of the supporting section 30, or the like by means of a control model formed based upon the coordinate (Xb, Yb) of the cervical spine A, and correction imaging of the cervical spine is performed for alleviating the influence of the cervical spine A on an imaging result. At the time of performing CT imaging, the CPU 71 controls the X-axis motor 60x and the Y-axis motor 60y, so as to shift the rotation central axis of the rotation of the X-ray generating section 10 and the X-ray image capturing section 20 in CT imaging to the coordinate (Xa, Ya). It is to be noted that the X-axis motor 60x, the Y-axis motor 60y and the CPU 71 constitute a rotation central axis shifting section. Further, the control model is set in consideration of the central coordinate (Xa, Ya) of the CT imaging area. This is because, even with the same coordinate (Xb, Yb) of the cervical spine A, if the central coordinate (Xa, Ya) of the CT imaging area is different, a position of the cervical spine A crossing a line between the X-ray generating section 10 and the X-ray image capturing section 20 is different.

Figure 4:
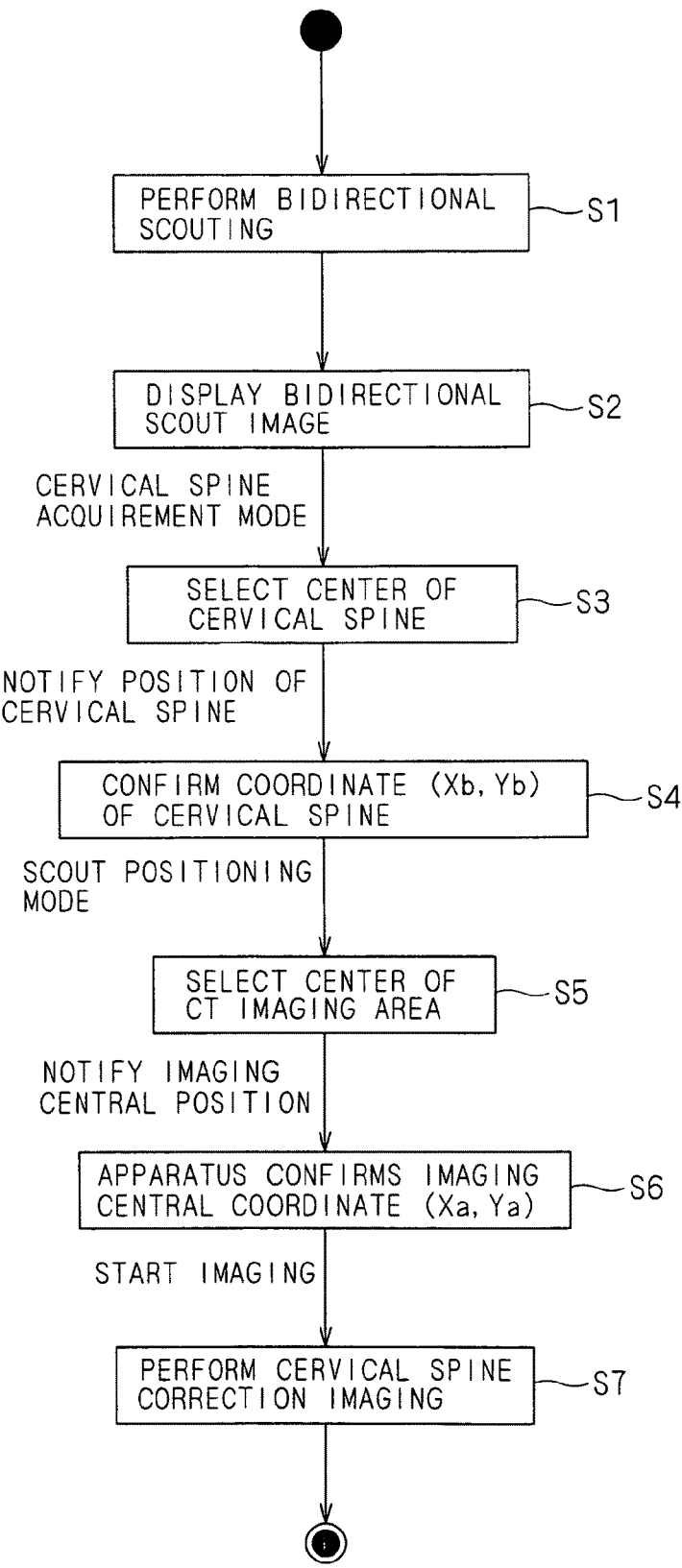
FIG. 4 is a flowchart explaining an operation of the X-ray CT imaging apparatus according to Embodiment 1.
Figure 5:
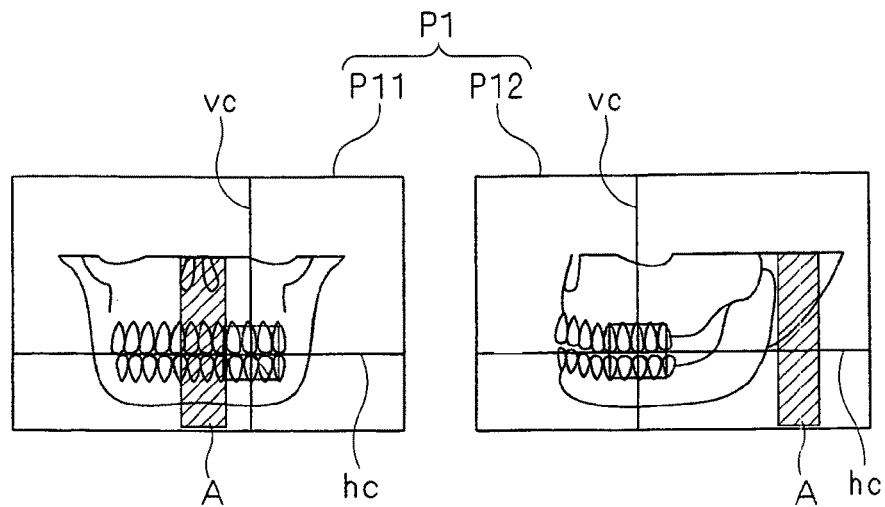
FIG. 5 is a view showing a scout image for use in the X-ray CT imaging apparatus according to Embodiment 1.
Figure 6:
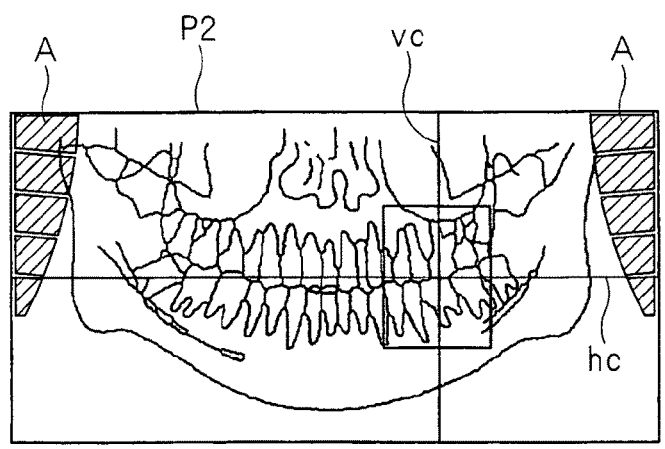
FIG. 6 is a view showing a panorama scout image for use in the X-ray CT imaging apparatus according to Embodiment 1.

In the flowchart shown in FIG. 4, the processing for recognizing the coordinate (Xb, Yb) of the cervical spine A by use of the bidirectional X-ray scout image has been shown, but the present invention is not limited thereto, and for example, a panorama scout image P2 shown in FIG. 6 may be used. In the panorama scout image P2 shown in FIG. 6, the cervical spine A is reflected in the right and left of the image, and hence designating this position by means of the mouse or the like can recognize the coordinate (Xb, Yb) of the cervical spine A. Further, also in the panorama scout image P2 shown in FIG. 6, the cursors hc, vc are shifted by use of the mouse or the like, to select the center of the CT imaging area. As an example of using the panorama scout image, such a configuration as in Patent Application Republication No. W2003-084407 according to an application of the present applicant can be considered. Further, a scout image for use in the processing for recognizing the coordinate (Xb, Yb) of the cervical spine A is not necessarily an X-ray image, but an image taken by visible rays may be used so long as the position of the cervical spine A can be selected. Further, although the bidirectional X-ray scout image is used in the flowchart shown in FIG. 4, a unidirectional X-ray scout image may also be used.

Next, the control model processed by the X-ray controlling section 82 is described. This control model shows a pattern (profile) of the X-ray controlling section 82 controlling the X-ray generating section 10, the rotation motor 60r and the like so as to alleviate the influence of the high X-ray absorption region (e.g. the cervical spine A) in the X-ray image capturing section 20 at the time of the region crossing over the line connecting the X-ray generating section 10 and the X-ray image capturing section 20. It is to be noted that as the control of the X-ray controlling section 82 alleviating the influence of the region in the X-ray image capturing section 20, control of increasing an X-rays output from the X-ray generating section 10 at the time of crossing of the cervical spine A or control of slowing a rotational speed of the rotation motor 60r at that time can be considered. However, the present invention is not limited thereto, and a method of controlling a configuration to shield X-rays outputted from the X-ray generating section 10 may be performed so long as the control alleviates the influence of the region in the X-ray image capturing section 20.

As for the configuration to shield the X-rays outputted from the X-ray generating section 10 considered can be a configuration to provide on the front surface of the X-ray generating section 10 a shutter-shaped X-ray shielding member, not shown, the opening/closing of which can be driven by a driving mechanism making use of an electromagnetic actuator or the like, or some other configuration. Controlling a ratio between the opening time and the shielding time (hereinafter referred to as an opening/closing time ratio) in the opening/closing operation by the driving mechanism controls a total time per unit time which is taken for the X-ray shielding member to shield the irradiated X-rays. For example, a configuration is formed such that the shielding time for shielding the irradiated X-rays is short in the portion crossing the high X-ray absorption region, and the shielding time for shielding the irradiated X-rays is long in the portion not crossing the high X-ray absorption region.

X-rays may be irradiated in a pulse shape so as to control a frequency or a pulse width thereof.

In the following, the operation of the X-ray CT imaging apparatus according to the present embodiment is described by taking a control model for controlling X-rays outputted from the X-ray generating section 10 as an example. First, FIG. 7 shows a flowchart of the X-ray controlling section 82 processing the control model. In Step S11 shown in FIG. 7, the X-ray controlling section 82 loads from the storage section 83 a ray amount profile table (X-ray output profile) as a control model corresponding to a rotational angle (in increments of one degree) of an arm (supporting section 30). In Step S11, the rotational angle of a starting position of the ray amount profile table is set to (mAPtr).

Next, in Step S12, the central coordinate (Xa, Ya) of the CT imaging area and the coordinate (Xb, Yb) of the cervical spine A are loaded to the X-ray controlling section 82. Then, in Step S12, "θ=atan((Xa−Xb)/(Ya−Yb))" is calculated ("atan" denotes an arctangent). Here, a median line is apprehended as the Y-axis and an angle θ to the median line is obtained. Next, in Step S13, the starting position read from the ray amount profile table is corrected. Namely, a value of (mAPtr) is delayed only by θ degrees (mAPtr−θ=mAPtr). This is processing where the X-ray irradiation is started with the starting position held in the position read from the ray amount profile table when the position in which the coordinate (Xb, Yb) of the cervical spine A is present with respect to the central coordinate (Xa, Ya) of the CT imaging area agrees with a position initially set in the ray amount profile table, but when the position is positionally displaced from the set position and directionally different by an angle of θ, correction corresponding thereto is added. For the sake of making this understood, a description is given by use of later-mentioned FIG. 8 though being an extreme example. Although a ray amount profile table with a position of FIG. 8(a) regarded as an X-ray irradiation starting position is prepared, it is assumed that an actual X-ray irradiation starting position is a position of FIG. 8(b). In that case, starting X-ray irradiation with an X-ray output indicated by a chain double-dashed line of FIG. 8(b) leads to appropriate control.

Next, based upon the conditions set in Steps S11 to S13, the rotational arm is rotated, to start X-ray irradiation. In Step S14, the X-ray controlling section 82 controls the X-ray generating section 10 so as to output an tube current corresponding to the ray amount profile table, thereby to control an X-ray amount to be outputted. Namely, "Table[mAPtr]=XmA" is set, and subsequently, mAPtr is advanced by one (i.e. by a value corresponding to a rotational angle of the rotational arm during a repetition period of S14) (mAPtr+1=mAPtr, mAPtr on the right side is a new mAPtr after advancement by one from mAPtr on the left side.) Next, in Step S15, it is determined whether or not the position of the rotational arm has reached a stopping position, and X-ray irradiation is continued in the case of the stopping position having not been reached, and the process advances to Step S16 to stop the X-ray irradiation in the case of the stopping position having been reached. As described later, it may be previously arranged to allow selection of a control model by size (body type) of an object (patient).

Figure 8:
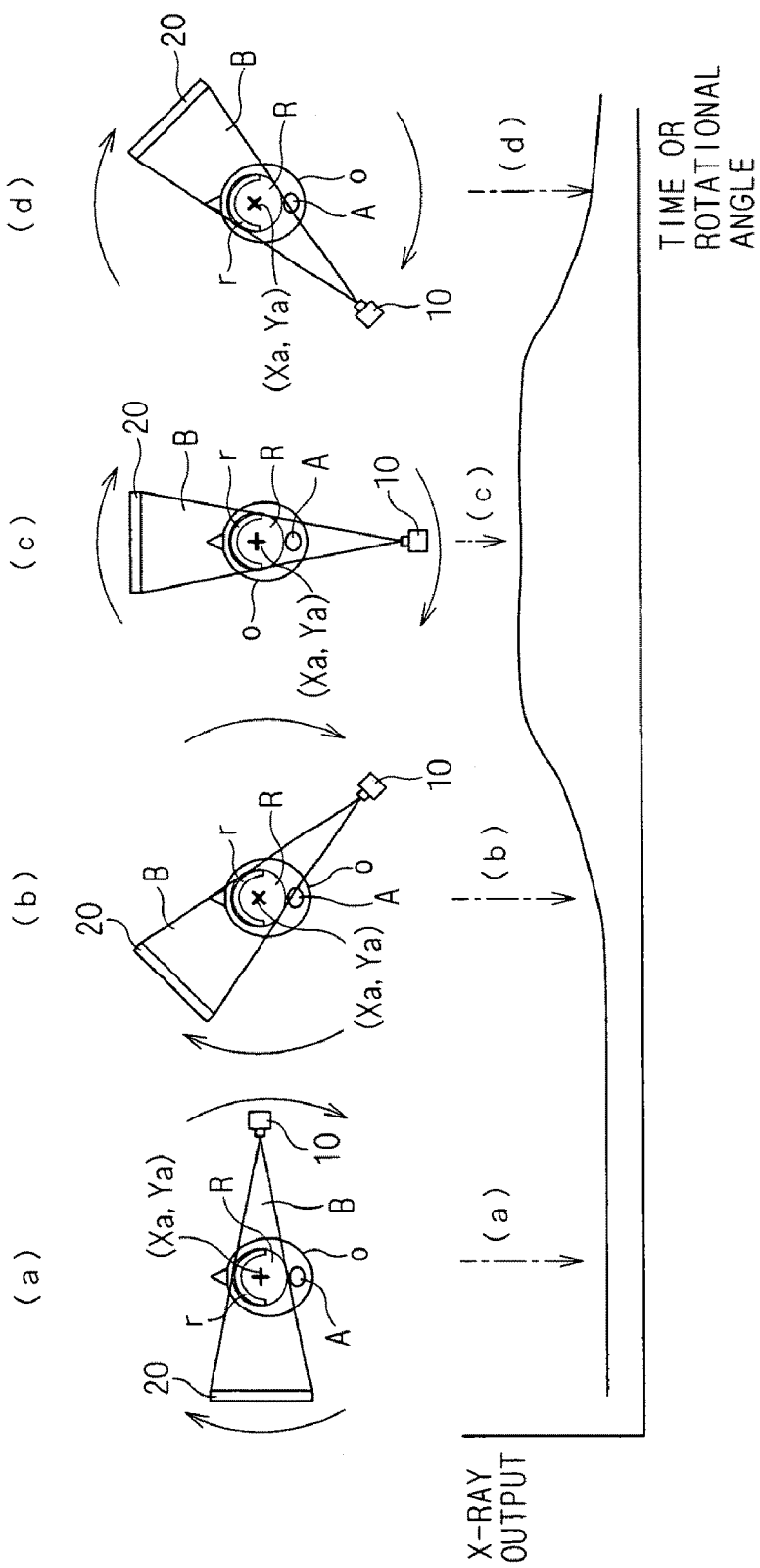
FIGS. 8 and 9 are views each for explaining the operation of the X-ray CT imaging apparatus according to Embodiment 1.
Figure 9:
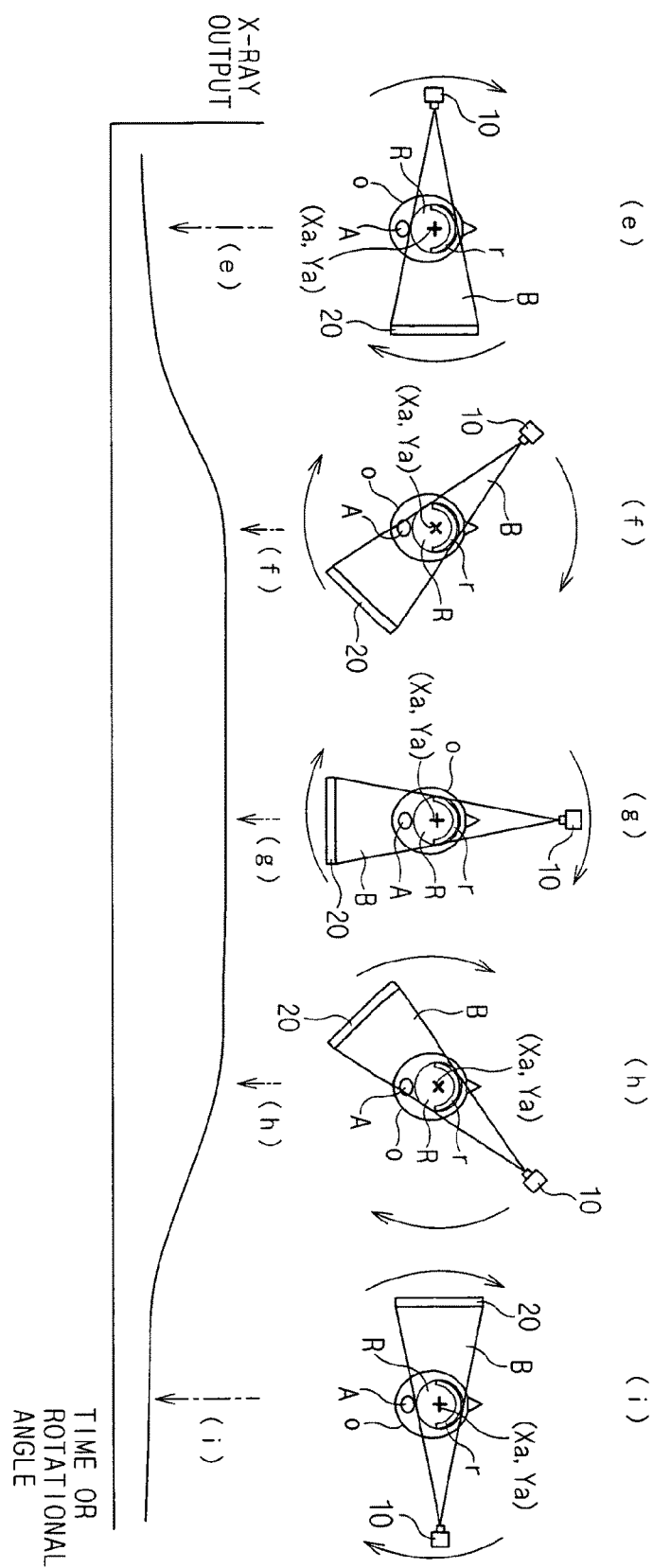

FIGS. 8 and 9 show views each showing a positional relation among the X-ray generating section 10, the X-ray image capturing section 20 and the cervical spine A, and a profile of an X-ray output. First, in FIG. 8(a), the X-ray cone beam B is applied from the X-ray generating section 10 such that the whole of a dental arch r of the object o is regarded as a CT imaging area R, and the X-ray cone beam B transmitted through the CT imaging area R is detected in the X-ray image capturing section 20. Further, the X-ray generating section 10 and the X-ray image capturing section 20 are rotated around the central coordinate (Xa, Ya) as the rotation central axis. In FIG. 8(a), since the X-ray generating section 10 and the X-ray image capturing section 20 are located in a position where the X-ray cone beam B does not intersect with the cervical spine A, the X-ray cone beam B passes through only the CT imaging area R, to reach the X-ray image capturing section 20. Therefore, when the positions of the X-ray generating section 10 and the X-ray image capturing section 20 are those in FIG. 8(a), the cervical spine A does not have an influence on an imaging result, and hence an amount of X-rays outputted from the X-ray image capturing section 20 can be held low.

It should be noted that in the case of controlling the X-ray output from the X-ray generating section 10, the X-ray output can be controlled by a tube current or a tube voltage that is supplied to the X-ray generating section 10.

When the X-ray generating section 10 and the X-ray image capturing section 20 are located in positions of FIG. 8(b), since part of the X-ray cone beam B intersects with the cervical spine A, the X-ray output is made large as compared with the case of FIG. 8(a) in order to alleviate the influence of the cervical spine A exerted on the imaging result. When the X-ray generating section 10 and the X-ray image capturing section 20 are located in positions of FIG. 8(c), since the X-ray cone beam B intersects with the whole of the cervical spine A, the X-ray output is made further large as compared with the case of FIG. 8(b) in order to alleviate the influence of the cervical spine A exerted on the imaging result. When the X-ray generating section 10 and the X-ray image capturing section 20 are located in positions of FIG. 8(d), since part of the X-ray cone beam B intersects with the cervical spine A, the X-ray output is made small as compared with the case of FIG. 8(c) (to the same extent as the case of FIG. 8(b)) in order to alleviate the influence of the cervical spine A exerted on the imaging result. It is to be noted that in the X-ray output profile shown in FIG. 8, a vertical axis indicates the X-ray output and a horizontal axis indicates the imaging time or the rotational angle.

Further, when the X-ray generating section 10 and the X-ray image capturing section 20 are located in positions of FIG. 9(e), since the X-ray cone beam B does not intersect with the cervical spine A, it is not necessary to alleviate the influence of the cervical spine A exerted on the imaging result, and hence the X-ray output is made further small as compared with the case of FIG. 8(c) (to the same extent as the case of FIG. 8(a)). When the X-ray generating section 10 and the X-ray image capturing section 20 are located in positions of FIG. 9(f), since the X-ray cone beam B intersects with most part of the cervical spine A, the X-ray output is made large as compared with the case of FIG. 9(e) (to the extent that the output is made slightly small as compared with the case of FIG. 8(c)) in order to alleviate the influence of the cervical spine A exerted on the imaging result. When the X-ray generating section 10 and the X-ray image capturing section 20 are located in positions of FIG. 9(g), since the X-ray cone beam B intersects with the whole of the cervical spine A, the X-ray output is made to the same extent as the case of FIG. 8(c) in order to alleviate the influence of the cervical spine A exerted on the imaging result. When the X-ray generating section 10 and the X-ray image capturing section 20 are located in positions of FIG. 9(h), since the X-ray cone beam B intersects with most of the cervical spine A, the X-ray output is made slightly small as compared with the case of FIG. 9(g) (to the same extent as the case of FIG. 9(f)) in order to alleviate the influence of the cervical spine A exerted on the imaging result. When the X-ray generating section 10 and the X-ray image capturing section 20 are located in positions of FIG. 9(i), since the X-ray cone beam B does not intersect with the cervical spine A, it is not necessary to alleviate the influence of the cervical spine A exerted on the imaging result, and hence the X-ray output is made small as compared with the case of FIG. 9(h) (to the same extent as the case of FIG. 8(a)). In addition, the positions of the X-ray generating section 10 and the X-ray image capturing section 20 are positions after one rotation of the rotational arm around the rotation central axis (Xa, Ya) from the positions of the X-ray generating section 10 and the X-ray image capturing section 20 in FIG. 8(a).

As thus described, in the X-ray CT imaging apparatus M according to the present embodiment, since the X-ray controlling section 82 controls the X-ray image capturing section 20 to alleviate the influence of the high X-ray absorption region present inside the object o by means of the control model based upon information on the region, it is possible to perform CT imaging in which the influence of the region is alleviated with a simple configuration at low cost.

Further, according to this X-ray CT imaging apparatus M, since an amount of X-rays that are applied to the X-ray irradiation object region affected by the high X-ray absorption region such as the cervical spine A is increased while the amount of X-rays that are applied to the X-ray irradiation object region not affected is held low, it is possible to hold an X-ray dose given to the object o as a whole while making a CT image clear.

In effect, the influence of the cervical spine A is large, and according to a measurement conducted by the applicant, appropriately reducing the X-ray amount in respect of the X-ray irradiation object region not affected by the cervical spine A can hold a sum total amount of X-rays required for imaging at about sixty percent of that in the case of imaging with a uniform X-ray amount.

Further, an output signal level may become saturated in the X-ray irradiation object region when an excess output amount of X-rays are applied to this region despite being not affected by the cervical spine A, whereas an output signal level regarding regions other than the cervical spine A may become short when an insufficient output amount of X-rays are applied to the X-ray irradiation object region despite being affected by the cervical spine A, but according to the present configuration, a density difference in an image within a dynamic range of the X-ray detector can be clarified, namely, a dynamic range of the CT image can be expanded.

Further, in the X-ray CT imaging apparatus M according to the present embodiment, the X-ray cone beam B further includes the X-ray transmission amount monitoring section (e.g. a predetermined detection section of the X-ray image capturing section 20 is used) for monitoring an amount of transmitted X-rays in a place constantly irradiated with the X-ray cone beam B, and hence the X-ray transmission amount monitoring section can correct the control model to make the monitored amount of transmitted X-rays a substantially constant value, so as to alleviate the influence of the region. Here, as the place constantly irradiated with the X-ray cone beam B, for example, a point under a nose of the object o can be focused on, and an amount of X-rays passing through the point under the nose can be monitored with the X-ray image capturing section 20 used as the X-ray transmission amount monitoring section.

It should be noted that in the X-ray CT imaging apparatus M according to the present embodiment, as in the flowchart shown in FIG. 4, processing of separately taking a scout image (Step S1) is performed before CT imaging, but the present invention is not limited thereto. For example, a scout image, a panorama scout image or the like previously taken can be read from the storage section 83 and used in CT imaging performed by the X-ray CT imaging apparatus M according to the present embodiment. Further, the scout image or the like previously taken may be one stored in the storage section 83 that is managed with respect to each object o, or may be one stored in an external medium which is associated with the X-ray CT imaging apparatus M.

Embodiment 2

In the X-ray CT imaging apparatus M according to Embodiment 1, it was necessary for obtaining high X-ray absorption region information to designate the region displayed on the scout image or the like by the operation section 86. On the other hand, in an X-ray CT imaging apparatus M according to the present embodiment, information on the region which is displayed on a scout image or the like is acquired through use of image pattern recognition.

Figure 10:
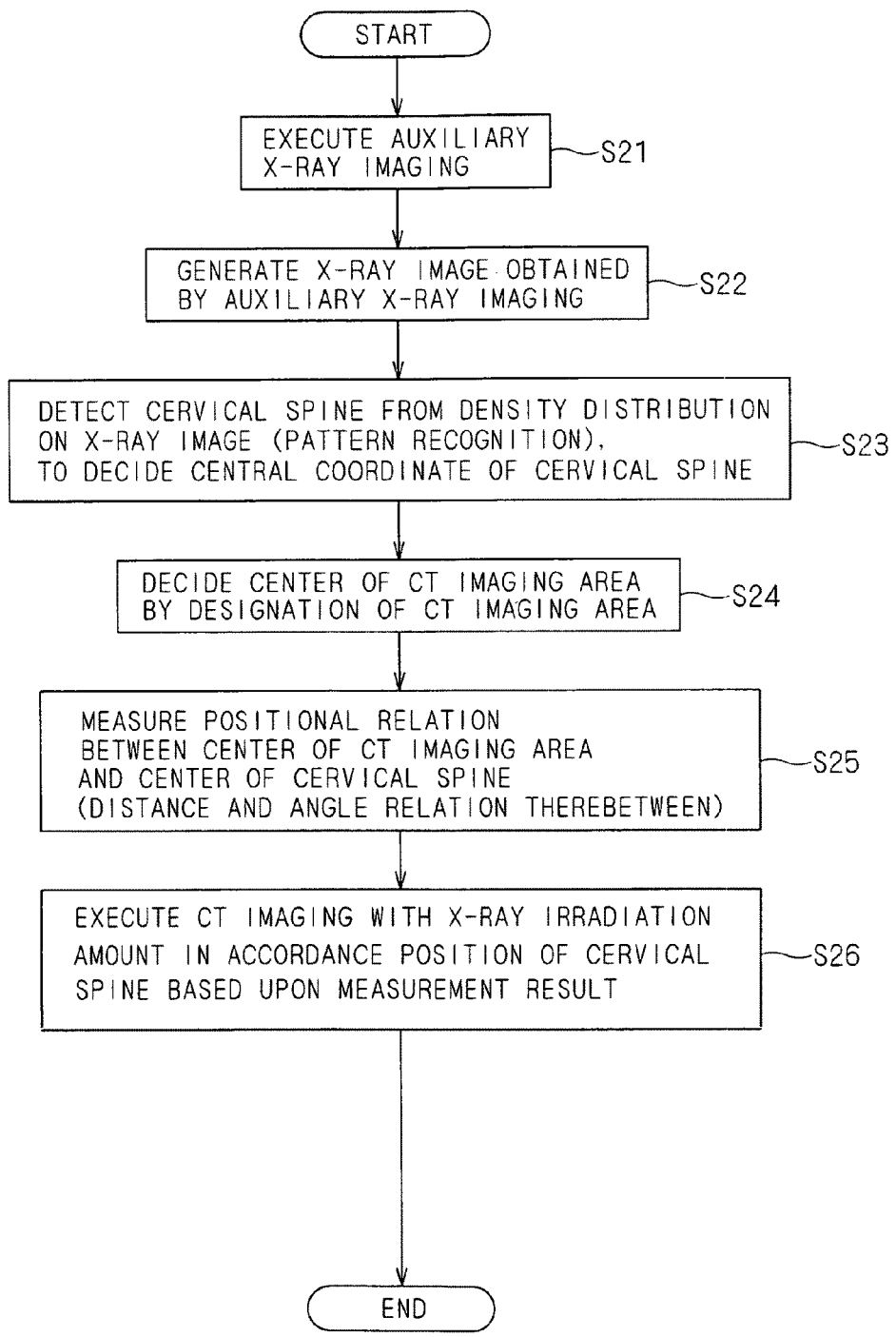
FIG. 10 is a flowchart explaining an operation of an X-ray CT imaging apparatus according to Embodiment 2.

Specifically, an operation of the X-ray CT imaging apparatus M according to the present embodiment is described by use of a flowchart shown in FIG. 10. First, in Step S21 shown in FIG. 10, auxiliary X-ray imaging is executed for obtaining a scout image or the like. It is to be noted that an image taken in the auxiliary X-ray imaging may be a single-shot fluoroscopic image, a bidirectional scout image, or a panorama scout image. Further, in Step S22, an X-ray image obtained in the auxiliary X-ray imaging is generated as in FIG. 11A.

Figure 11A:
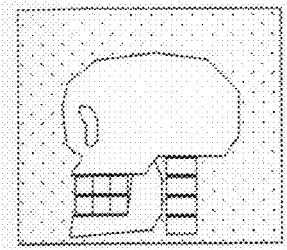
FIGS. 11A to 11C are views each for explaining image pattern recognition for use in the X-ray CT imaging apparatus according to Embodiment 2.
Figure 11B:
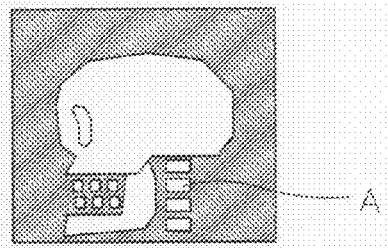
Figure 11C:
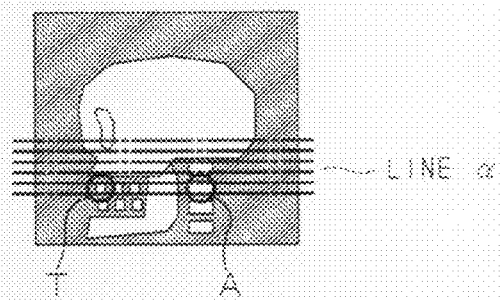

Next, in Step S23, the cervical spine A is detected from a density distribution on the X-ray image, to decide the central coordinate of the cervical spine A. As a method for recognizing the cervical spine A, image pattern recognition is used. As an example of the image pattern recognition, first, the image of FIG. 11A is changed into a binarized image as in FIG. 11B. Subsequently, the image is sequentially analyzed in a scanning manner, as shown with lines a of FIG. 11C, to recognize the cervical spine A. Further, the lateral center and longitudinal center of an area determined as the cervical spine A are set as the center of the cervical spine, and decided as the central coordinate (Xb, Yb) of the cervical spine A. In FIG. 11C, recognition of the teeth T or the cervical spine A can be determined from a size of a density portion or the like.

Figure 12:
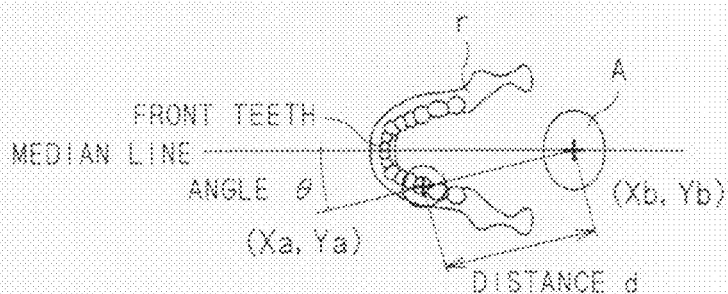
FIG. 12 is a view for explaining the operation of the X-ray CT imaging apparatus according to Embodiment 2.

Next, in Step S24, a CT imaging area is designated and the central coordinate (Xa, Ya) of the CT imaging area is decided. In Step S25, a positional relation is measured between the central coordinate (Xb, Yb) of the cervical spine A acquired in Step S23 and the central coordinate (Xa, Ya) of the CT imaging area acquired in Step S24. In addition, as shown in FIG. 12, the positional relation between both coordinates is a distance d between (Xa, Ya) and (Xb, Yb), or an angle θ formed by (Xa, Ya) with (Xb, Yb) as the center against a median line connecting the front teeth of the dental arch r and the cervical spine A. Next, in Step S26, according to the measurement result of Step S25, CT imaging is executed with an X-ray irradiation amount in accordance with the position of the cervical spine based upon the control model.

As thus described, in the X-ray CT imaging apparatus M according to the present embodiment, since the region information acquiring section 85 specifies the high X-ray absorption region from the scout image by image pattern recognition, an operator is not required to separately specify a position of the region, thereby enabling alleviation of the operation. Computing is performed based upon the central coordinate (Xb, Yb) of the cervical spine A for convenience of positional computing. Naturally, since the cervical spine is not essentially a point but has an expanded shape, from which angle the X-ray cone beam B starts being applied to the cervical spine A is calculated in consideration of a position of an outer edge of the cervical spine.

Embodiment 3

In an X-ray CT imaging apparatus M according to the present embodiment, a control model previously set based upon a size of the object o (patient) is selected to alleviate an influence of a high X-ray absorption region, to perform CT imaging.

Figure 13:
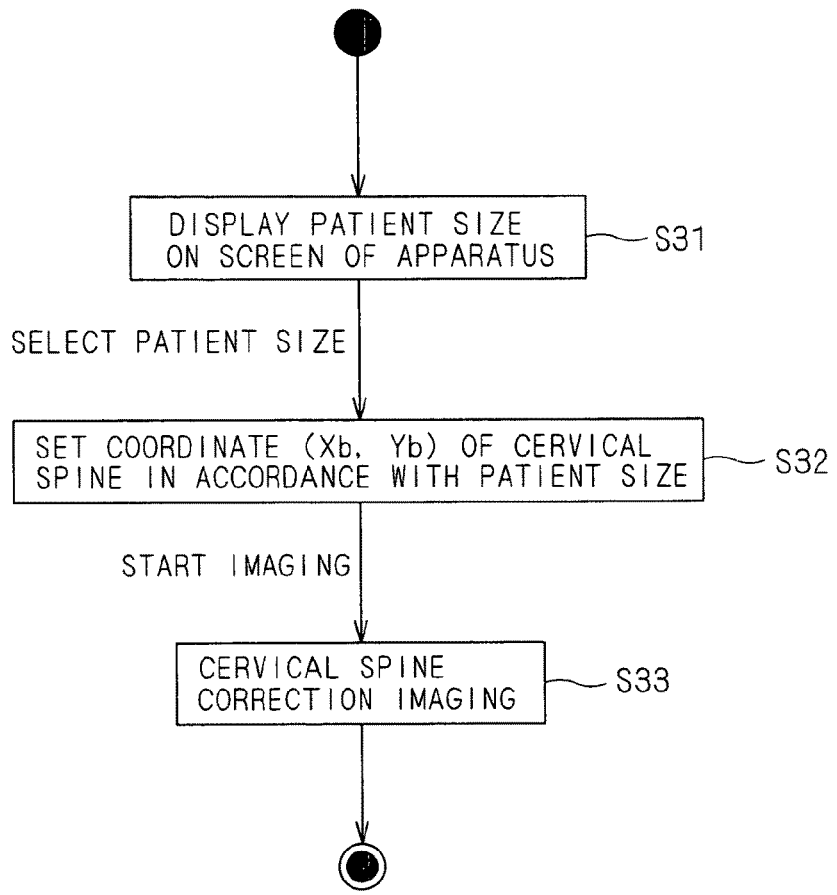
FIG. 13 is a flowchart explaining an operation of an X-ray CT imaging apparatus according to Embodiment 3.

Specifically, an operation of the X-ray CT imaging apparatus M according to the present embodiment is described by use of a flowchart shown in FIG. 13. First, in Step S31, an image shown in FIG. 14 is displayed on the operation panel 76 in FIG. 1 and the like. FIG. 14(a) is a screen with the CT imaging area R set to a diameter of 40 mm and a height of 40 mm, and "40×40" has been selected in a CT imaging area size selection button 741. Meanwhile, FIG. 14(b) is a screen with the CT imaging area R set to a diameter of 140 mm and a height of 100 mm, and "140×100" has been selected in the CT imaging area size selection button 741. Further, in FIGS. 14(a) and 14(b), a patient size (head size) has been set to "M" by means of a patient size selection button 742. In addition, it is configured that the patient size is selected from a plurality of alternatives such as "L", "M" and "S".

Next, in Step S32, based upon the selection of the patient size displayed in Step S31, the central coordinate (Xb, Yb) of the cervical spine A corresponding to the patient size is set (e.g. an average position of the cervical spine A corresponding to the M sized patient). Next performed is cervical spine correction imaging S33, which includes Steps S5, S6 shown in FIG. 4.

As described above, in the X-ray CT imaging apparatus M according to the present embodiment, since the region information acquiring section 85 selects the size (body type) of the object (patient) from predetermined alternatives to acquire the high X-ray absorption region information, another processing for specifying the region becomes unnecessary, which can simplify the operation. Particularly as compared with the case of performing X-ray imaging as auxiliary imaging to specify the region, the X-ray CT imaging apparatus M according to the present embodiment can reduce a dose given to the object.

It is to be noted that a cassette type can be adopted to an X-ray sensor constituting the X-ray image capturing section 20 of the X-ray CT imaging apparatus M. This cassette-type X-ray sensor is insertable into and removable from a cassette holder of the X-ray detection section 20 provided on one side of the rotational arm as the supporting section 30. A plurality of kinds of X-ray sensors with X-ray detection surfaces having different sizes are made insertable and removable as cassettes so as to be replaceable with respect to each purpose of CT imaging. For example, at the time of purchasing a CT apparatus, a low-cost X-ray sensor cassette having a small detection surface is purchased together, to perform only local CT imaging, and afterwards an X-ray sensor cassette having a large detection surface is purchased for extension, so as to perform whole chin CT imaging. Naturally, an X-ray sensor having a large detection surface may be initially prepared to make a CT imaging object area or a detection area changeable within the range of the detection surface, and the X-ray sensor may be one fixed to the X-ray image capturing section or configured to be the cassette type.

Figure 15:
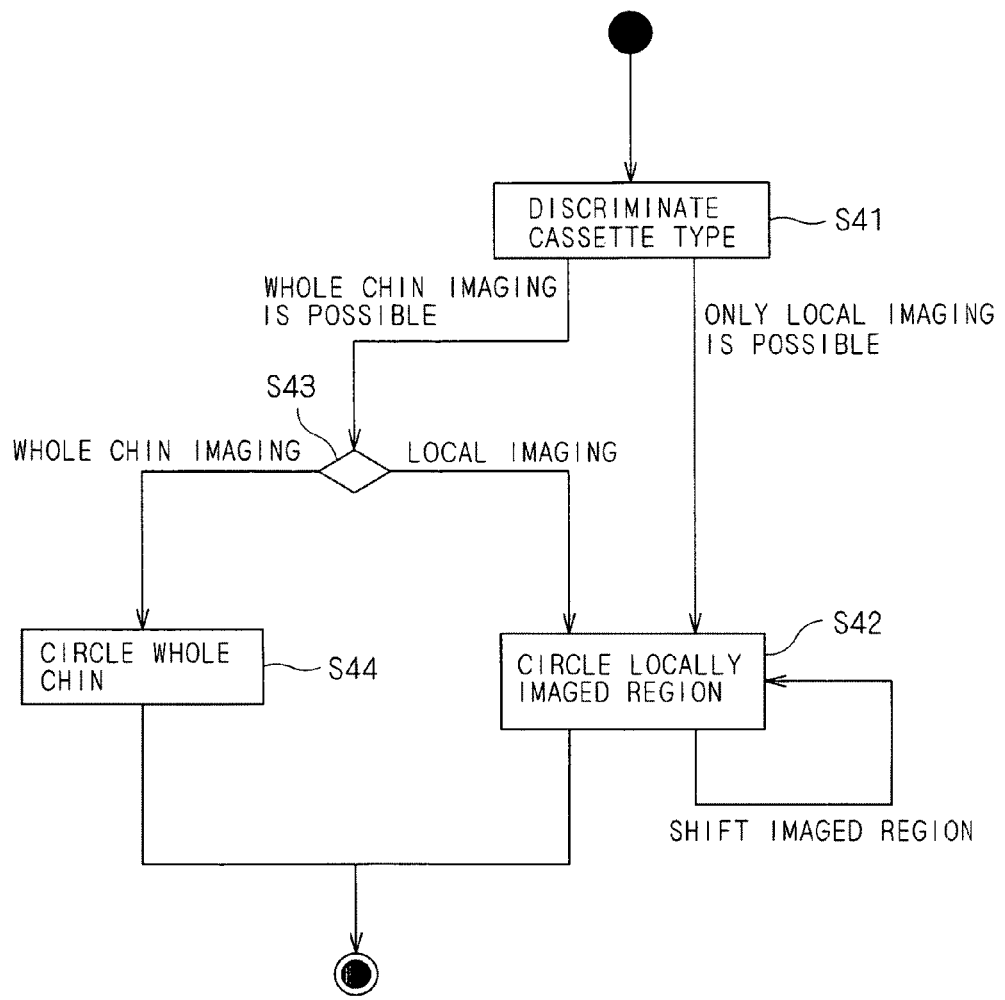
FIG. 15 is a flowchart explaining the operation of the X-ray CT imaging apparatus according to Embodiment 3.

When the X-ray CT imaging apparatus M with the X-ray sensor formed as a cassette so as to be replaceable is configured as described above, a flowchart for designation of the CT imaging area is as in FIG. 15. First, in Step S41, a cassette type is discriminated to determine whether the sensor is a large-sized X-ray sensor capable of whole-chin CT imaging or a small-sized X-ray sensor only for local CT imaging. When it is determined in Step S41 that the small-sized X-ray sensor has been installed, a locally imaged region is circled as the CT imaging area R in FIG. 14(a) (Step S42). Subsequently, the supporting section 30 is shifted to perform local CT imaging.

On the other hand, when it is determined in Step S41 that the large-sized X-ray sensor has been installed, whether to perform the whole chin imaging or the local imaging is selected in Step S43. When the local imaging is selected in Step S43, the process advances to Step S42. When the whole chin imaging is selected in Step S43, the process advances to Step S44, and the whole chin is circled as the CT imaging area R in FIG. 14(b).

Embodiment 4

In an X-ray CT imaging apparatus M according to the present embodiment, the object o is measured in order to obtain the high X-ray absorption region information.

Figure 16:
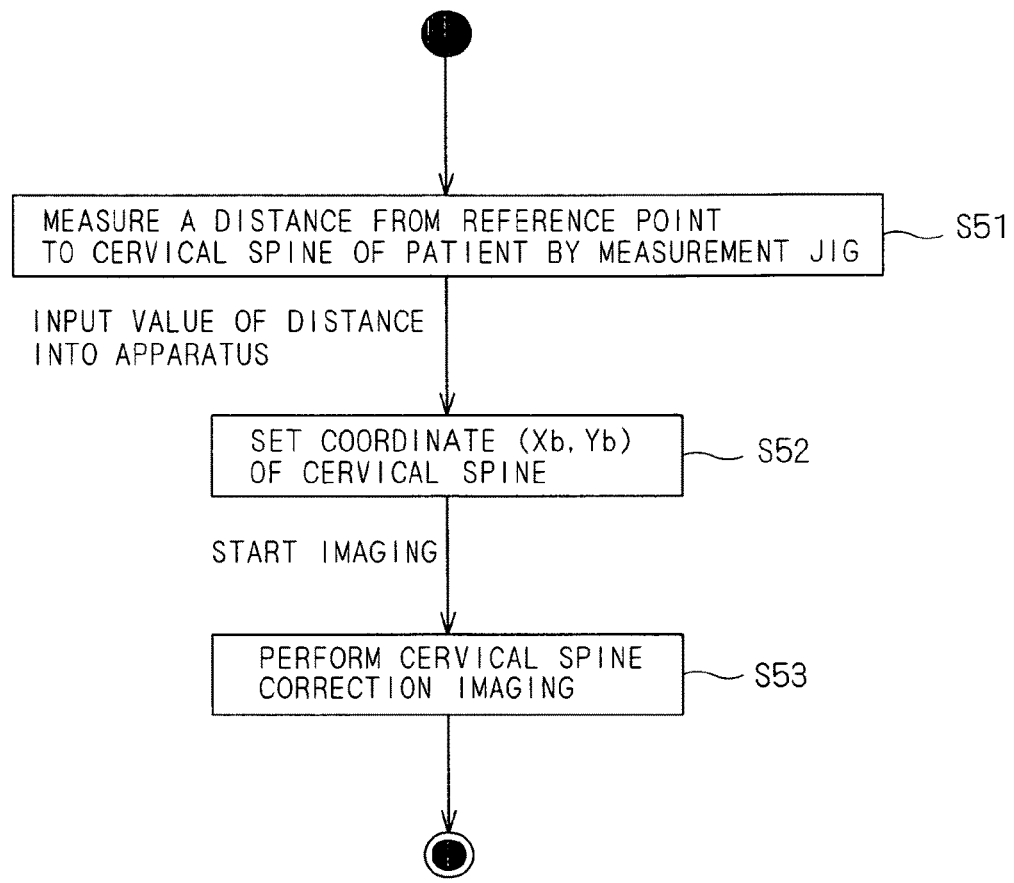
FIGS. 16 and 17 are flowcharts each explaining an operation of an X-ray CT imaging apparatus according to Embodiment 4.
Figure 17:
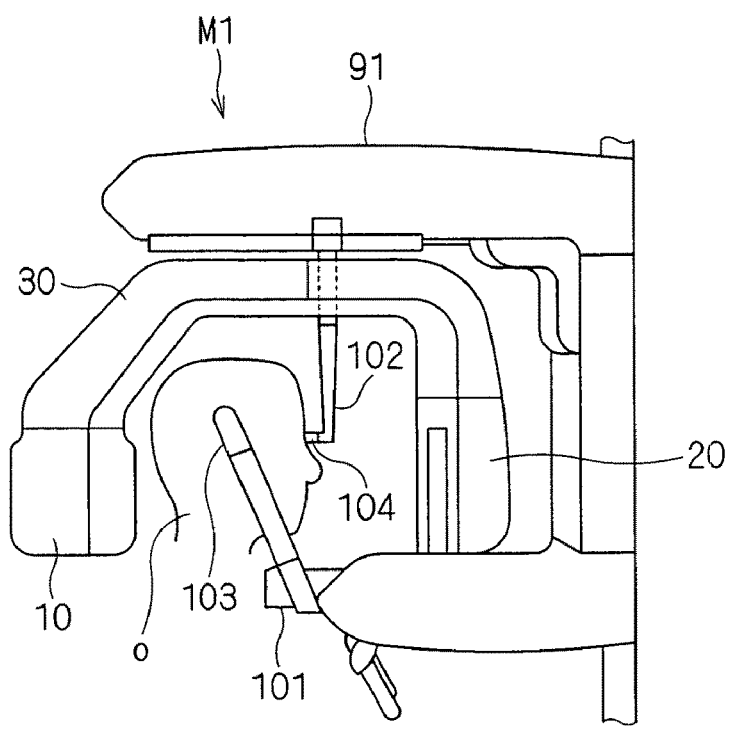

An operation of the X-ray CT imaging apparatus M according to the present embodiment is specifically described by use of a flowchart shown in FIG. 16. First, in Step S51, a distance from a reference point to the cervical spine A of the patient (object) is measured by means of a measurement jig. As the measurement jig considered can be a measurement jig installed on the X-ray CT imaging apparatus body M1 as shown in FIG. 17. The measurement jig shown in FIG. 17 includes a chin holding section 101, a forehead holding section 102, and a measurement arm section 103. The measurement jig shown in FIG. 17 measures a distance to the cervical spine by shifting the measurement arm section 103 to a position in the vicinity of the cervical spine of the patient (object o) with a contact point between the forehead holding section 102 and the patient (object o) regarded as a reference point. It is to be noted that the measurement jig shown in FIG. 17 also functions as the holding section 40 for holding the patient. A measurement jig, not shown, which measures a position of the rear end of a neck of a person to be imaged, such as a patient, held in the holding section 40 may be adopted. Since a distance from the rear end of the neck to the cervical spine doesn't vary much between individuals, the accuracy of positional detection becomes high.

Next, in Step S52, the result measured in Step S51 is inputted, and based upon the imaging result, the central coordinate (Xb, Yb) of the cervical spine is set. In addition, it may be configured that an input of the result measured in Step S51 is made automatically into the region information acquiring section 85 in synchronization with the measurement jig, or is made by use of the operation section 86. Further, the measurement jig is not necessarily mounted on the X-ray CT imaging apparatus body M1, but it may be configured that only a result measured using a measurement jig provided in another place is inputted into the region information acquiring section 85. Next performed is cervical spine correction imaging S53, which includes Step S5, S6 shown in FIG. 4.

As described above, in the X-ray CT imaging apparatus M according to the present embodiment, since the region information acquiring section 85 specifies the high X-ray absorption region information based upon data on measurement of the object, auxiliary imaging is unnecessary, which can reduce a load of the patient, and simplify the operation. Further, performing measurement of the object o by use of the holding section 40 can hold and measure the object o simultaneously.

Embodiment 5

In the X-ray CT imaging apparatus M according to the above embodiment, the configuration to perform CT imaging of the whole chin has been mainly described. On the other hand, in an X-ray CT imaging apparatus M according to the present embodiment, a configuration to perform local CT imaging is described.

Figure 18A:
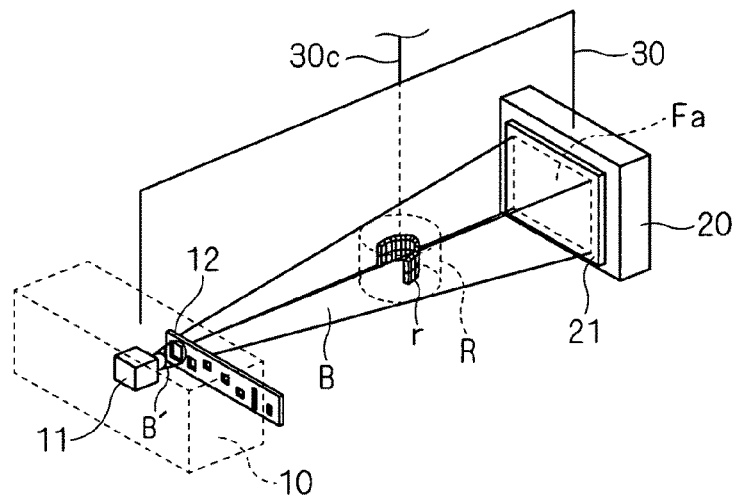
FIGS. 18A to 18C are views each for explaining whole chin CT imaging and local CT imaging in the X-ray CT imaging apparatus.
Figure 18B:
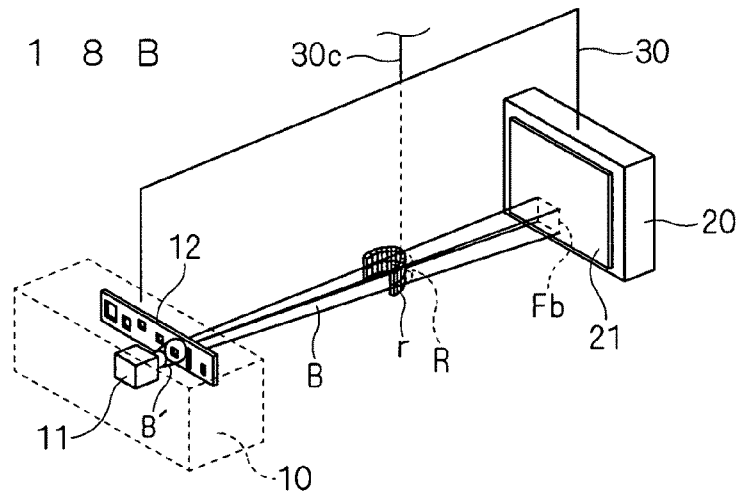
Figure 18C:
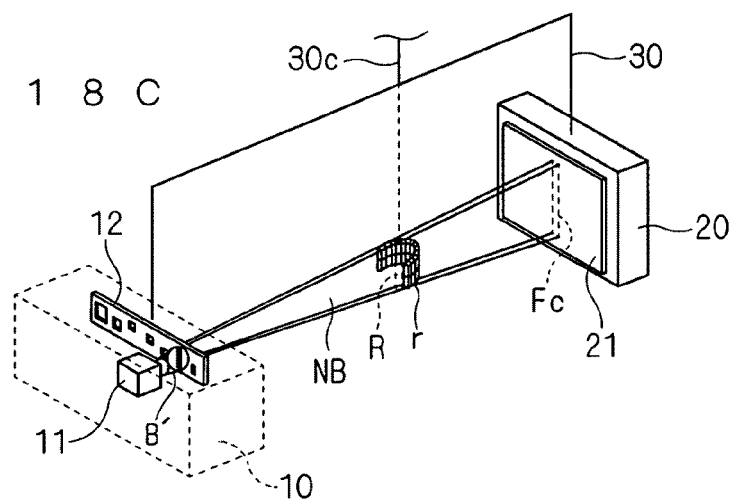

First, a difference between the whole chin CT imaging and the local CT imaging is described using FIGS. 18A, 18B and 18C. FIG. 18A is a schematic view explaining the whole chin CT imaging, and the expansion of the X-ray cone beam B' outputted from the X-ray generator 11 of the X-ray generating section 10 is controlled in the irradiation field controlling section 12 so as to give the X-ray cone beam B, which is applied to the whole chin including the dental arch r as the CT imaging area R and reaches the X-ray detector 21 of the X-ray image capturing section 20. In the whole chin CT imaging of FIG. 18A, the whole surface of the X-ray detector 21 becomes an irradiation area Fa of the X-ray cone beam B.

FIG. 18B is a schematic view explaining the local chin CT imaging, and the expansion of the X-ray cone beam B' outputted from the X-ray generator 11 of the X-ray generating section 10 is controlled in the irradiation field controlling section 12 so as to give the X-ray cone beam B with a smaller expansion than shown in FIG. 18A, which is applied to part of the dental arch r as the CT imaging area R and reaches the X-ray detector 21 of the X-ray image capturing section 20. In the local chin CT imaging of FIG. 18B, part of the X-ray detector 21 becomes an irradiation area Fb of the X-ray cone beam B. The local CT imaging is CT imaging of such a small irradiation field where, for example in the case of setting a dental arch as an imaging object, about two to four teeth are an imaging region.

FIG. 18C is a schematic view explaining panorama imaging, and the expansion of the X-ray cone beam B' outputted from the X-ray generator 11 of the X-ray generating section 10 is controlled in the irradiation field controlling section 12 (differently from the case of FIG. 18B, horizontal expansion is significantly controlled), which is applied to part of the dental arch r in accordance with a conventional technique for panorama imaging, and reaches the X-ray detector 21 of the X-ray image capturing section 20. In the imaging of FIG. 18C, part of the X-ray detector 21 becomes an irradiation area Fc of a slit X-ray beam NB. In the panorama imaging, typically, the slit X-ray cone beam NB is applied so as to form an envelope when seen from above, and in order to realize its path, X-rays are applied during imaging while the X-axis motor 60x and the Y-axis motor 60y shift the rotation central axis 30c of the supporting section 30 simultaneously with rotation of the X-ray generating section 10 and the X-ray image capturing section 20. It is to be noted that FIG. 18C represents a state of the slit X-ray cone beam NB being applied to the vicinity of the center of the front teeth.

Although the local CT imaging such as those in FIGS. 18B and 18C is described in the X-ray CT imaging apparatus M according to the present embodiment, since a configuration and an operation of a basic apparatus are the same as the configuration and the operation of the X-ray CT imaging apparatus M described in the foregoing embodiment, detailed explanations are omitted. In the following, characteristic respects in the local CT imaging are described.

Figure 19:
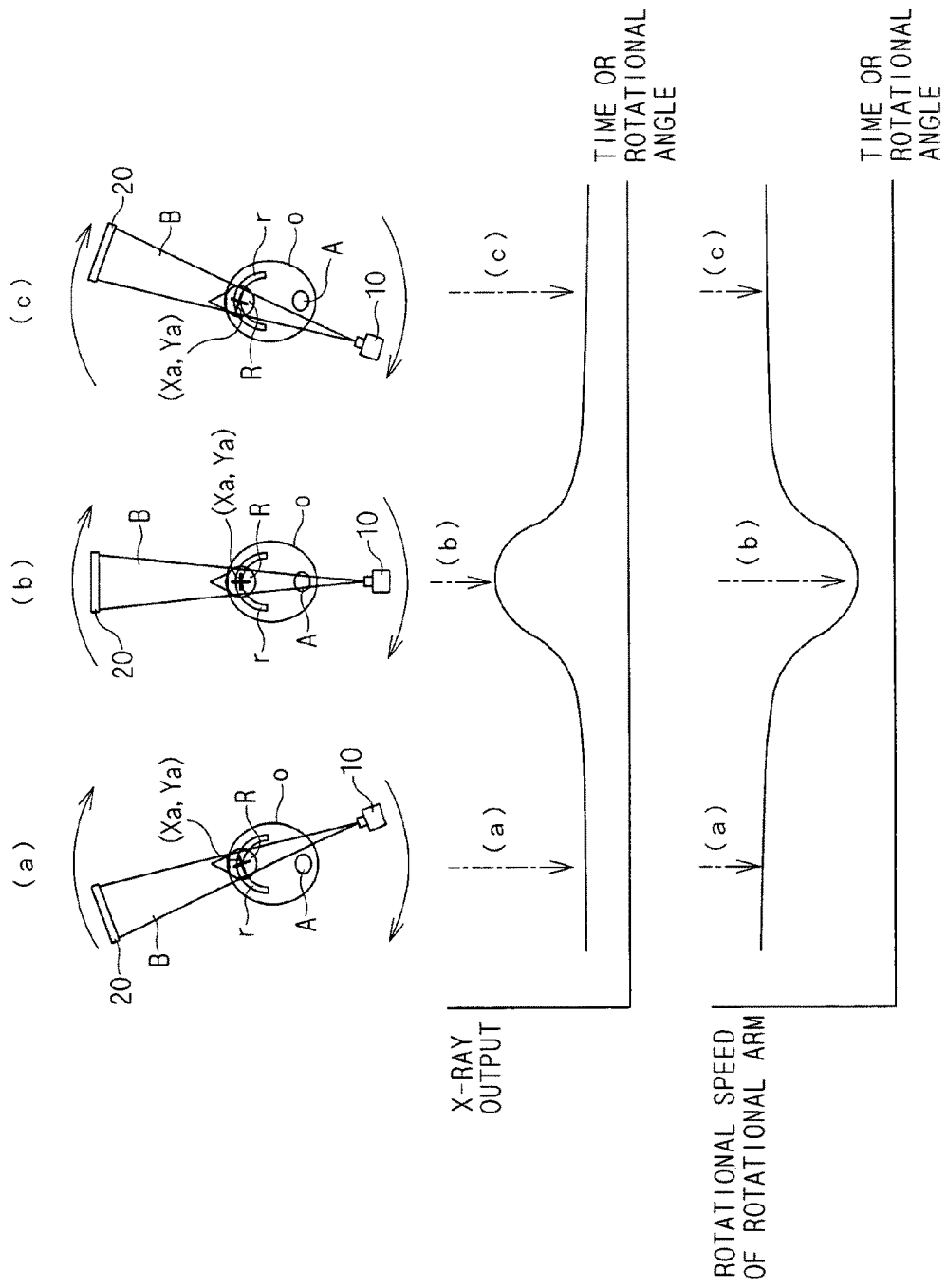

First, FIG. 19 shows a positional relation of the X-ray generating section 10, the X-ray image capturing section 20 and the cervical spine A and profiles of an X-ray output and a rotational speed of the rotational arm in the X-ray CT imaging apparatus M according to the present embodiment.

In FIG. 19, a graph with a vertical axis indicated as "X-ray output" is a profile of the X-ray output, and a graph with a vertical axis indicated as "Rotational speed of rotational arm" is a profile of the rotational speed of the rotational arm. As thus described, this figure shows that both control by the X-ray output and control by the rotational speed of the rotational arm can be performed. While either the control by the X-ray output or the control by the rotational speed of the rotational arm may be performed, both controls may be performed to give an appropriate X-ray irradiation amount.

In FIG. 19, the X-ray cone beam B is applied from the X-ray generating section 10 so as to regard part (the front teeth) of the dental arch r of the object o as the CT imaging area R, and the X-ray cone beam B having been transmitted through the CT imaging area R is detected in the X-ray image capturing section 20. Further, the X-ray generating section 10 and the X-ray image capturing section 20 are rotated around the central coordinate (Xa, Ya) as the rotation central axis. In FIG. 19(a), since the X-ray generating section 10 and the X-ray image capturing section 20 are located in positions where the X-ray cone beam B does not intersect with the cervical spine A, the X-ray cone beam B is transmitted only through the CT imaging area R and reaches the X-ray image capturing section 20. Therefore, in the case of the X-ray generating section 10 and the X-ray image capturing section 20 being located in positions of FIG. 19(a), since the cervical spine A does not have an influence on an imaging result as shown in the X-ray output profile, an amount of X-rays outputted by the X-ray image capturing section 20 can be held low. Further, in the case of FIG. 19(a), since the cervical spine A does not have an influence on the imaging result as shown in the rotational speed profile, the rotational speed of the rotational arm (supporting section 30) can be made high.

In the case of the X-ray generating section 10 and the X-ray image capturing section 20 being located in positions of FIG. 19(b), since the X-ray cone beam B intersects with part of the cervical spine A, the X-ray output is made large as compared with the case of FIG. 19(a) in order to alleviate the influence of the cervical spine A exerted on the imaging result. Further, in the case of FIG. 19(b), the rotational speed of the rotational arm is made low as compared with the case of FIG. 19(a). In the case of the X-ray generating section 10 and the X-ray image capturing section 20 being located in positions of FIG. 19(c), since the X-ray cone beam B does not intersect with part of the cervical spine A and the cervical spine A thus does not have an influence on the imaging result, the X-ray output is made small as compared with the case of FIG. 19(b). Further, in the case of FIG. 19(c), the rotational speed of the rotational arm is made high as compared with the case of FIG. 19(b). It is to be noted that in the X-ray output profile shown in FIG. 19, a vertical axis indicates the X-ray output and a horizontal axis indicates the imaging time or the rotational angle. Moreover, in the profile of the rotational speed, a vertical axis indicates the rotational speed of the rotational arm and a horizontal axis indicates the imaging time or the rotational angle.

The X-ray output profile shown in FIG. 19 and the like are basically the same as configurations shown in FIG. 8 and the like in which the whole chin CT imaging is performed. However, in the case of the local CT imaging as in the present embodiment, the X-ray output profile and the like vary depending upon which position of the dental arch r is regarded as the CT imaging area R. Namely, with the X-ray output profile and the like varying, the control model varies in each local portion.

Figure 20:
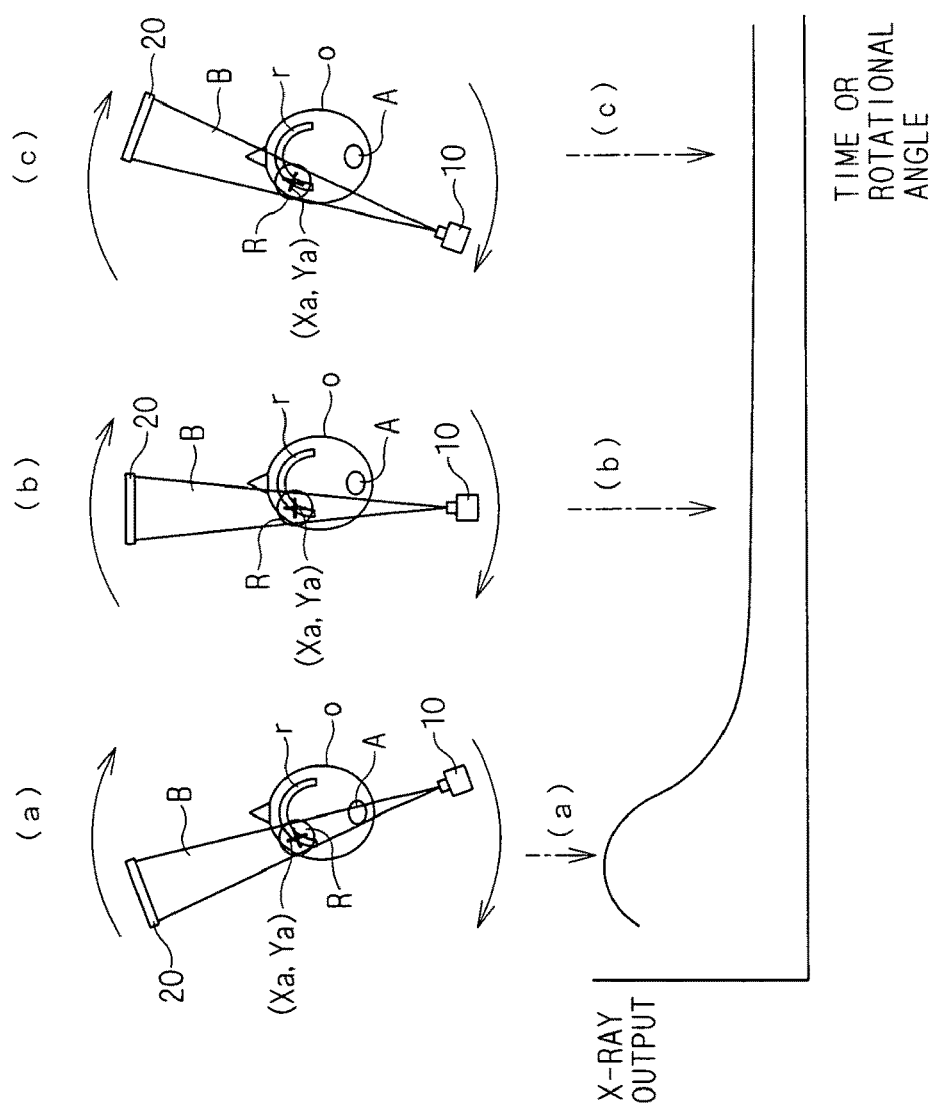

Specifically, FIG. 20 shows the positional relation of the X-ray generating section 10, the X-ray image capturing section 20 and the cervical spine A as well as the profile of the X-ray output in the case of performing local CT imaging of a position different from FIG. 19. In FIG. 20(a), since the X-ray generating section 10 and the X-ray image capturing section 20 are located in positions where the X-ray cone beam B intersects with the cervical spine A, the X-ray cone beam B passes through the cervical spine A and the CT imaging area R, to reach the X-ray image capturing section 20. Therefore, in the case of the X-ray generating section 10 and the X-ray image capturing section 20 being located in positions of FIG. 20(a), since the cervical spine A has an influence on an imaging result as shown in the X-ray output profile, an amount of X-rays outputted by the X-ray image capturing section 20 is made high.

In the case of the X-ray generating section 10 and the X-ray image capturing section 20 being located in positions of FIG. 20(b), since the cervical spine A does not intersect with the X-ray cone beam B and the cervical spine A thus does not have an influence on the imaging result, the amount of X-rays outputted by the X-ray image capturing section 20 is made low as compared with the case of FIG. 20(a). Also in the case of the X-ray generating section 10 and the X-ray image capturing section 20 being located in positions of FIG. 20(c), since the cervical spine A does not intersect with the X-ray cone beam B and the cervical spine A thus does not have an influence on the imaging result, the amount of X-rays outputted by the X-ray image capturing section 20 is made to the same extent as the case of FIG. 20(b). In the shown examples, the peak of the X-ray output appears in the state of FIG. 19(b) in FIG. 19, and in the state of FIG. 20(a) in FIG. 20.

A control model corresponding to the local portion of the object may be stored with respect to each local portion of the object or may be calculated from a standard control model.

Figure 21:
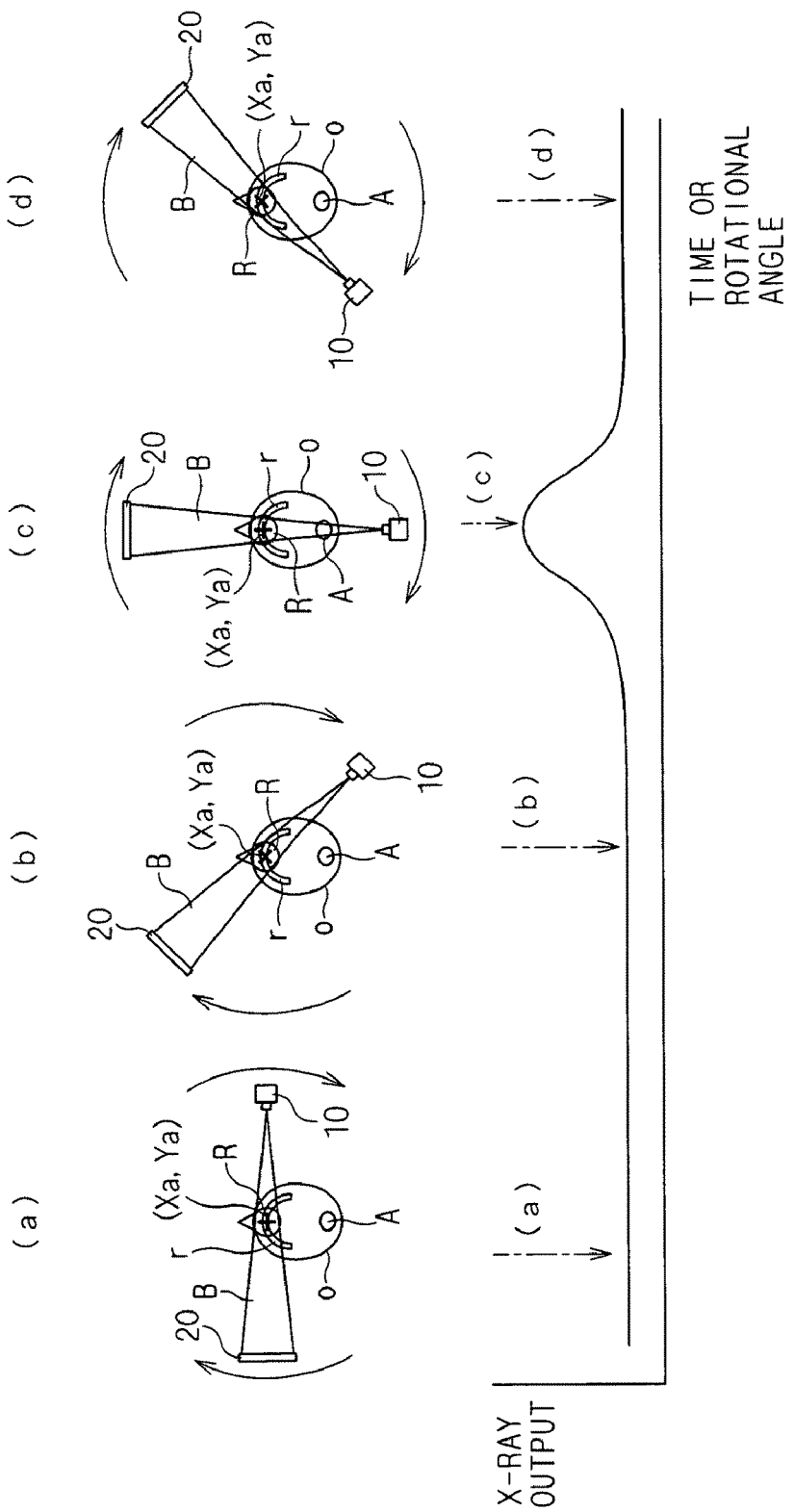
Figure 22:
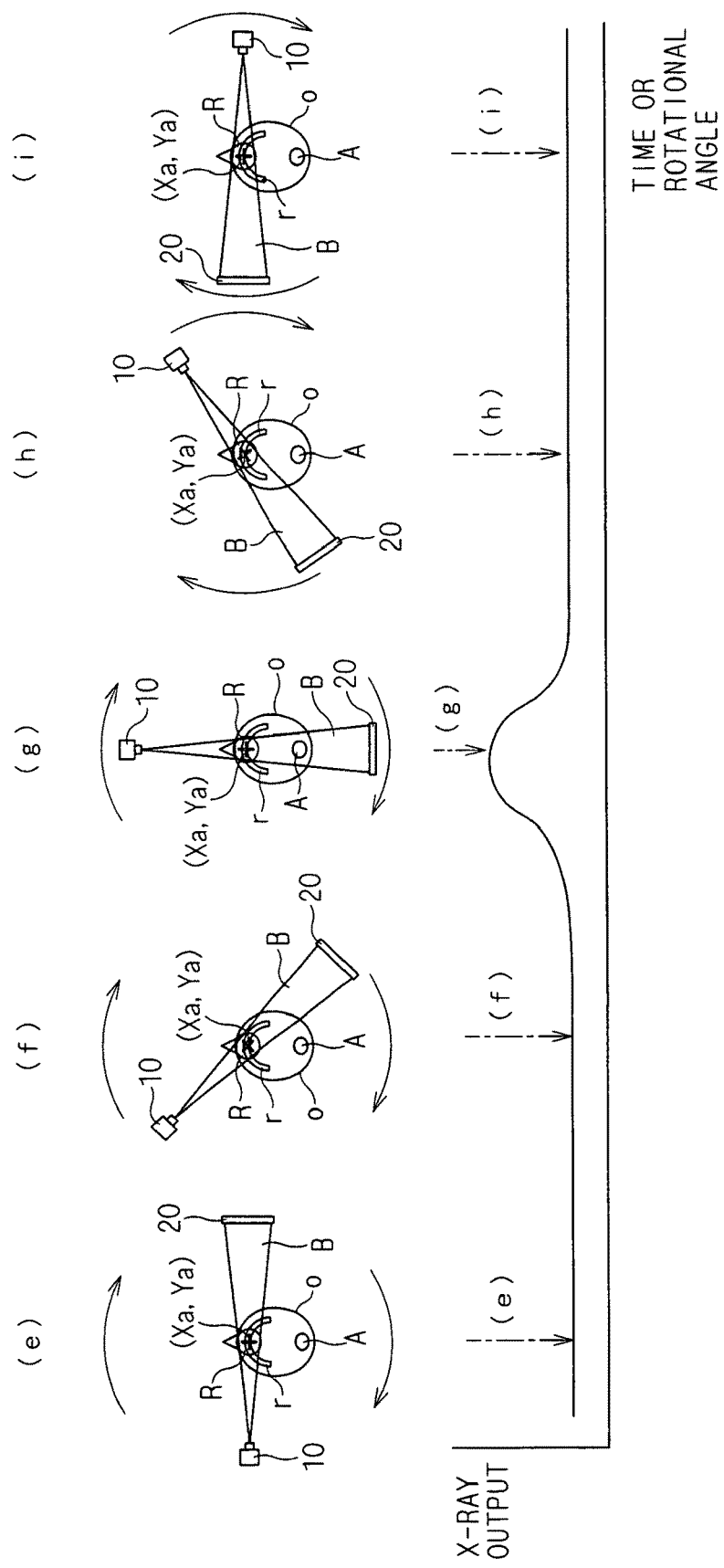

Further, in the case of the local CT imaging, the imaging is susceptible to the position of the cervical spine A as compared with the case of the whole chin CT imaging. For example described is an influence exerted on the X-ray output profile by a positional relation between the X-ray generating section 10 and the cervical spine A in the X-ray CT imaging apparatus M shown in FIGS. 21, 22. It is to be noted that, if FIGS. 21(a) to 21(d) and FIGS. 22(e) to 21(h) and 22(i) are described, the descriptions thereof would be almost the same as those of FIG. 8, and since the figures can be readily understood by the description of FIG. 19 or the like, the descriptions are omitted. However, FIG. 21(c) and FIG. 22(g) are described as below since having respects to be mentioned. In FIG. 21(c), since the X-ray generating section 10, the cervical spine A, the CT imaging area R and the X-ray image capturing section 20 are located in this order, a distance between the X-ray generating section 10 and the cervical spine A becomes short. Therefore, since the X-ray cone beam B from the X-ray generating section 10 reaches the cervical spine A without expanding much, most of the X-ray cone beam B intersects with the cervical spine A as shown in FIG. 21(c), thereby to have a large influence on the imaging result of the cervical spine A.

On the other hand, in FIG. 22(g), since the X-ray generating section 10, the CT imaging area R, the cervical spine A and the X-ray image capturing section 20 are located in this order, a distance between the X-ray generating section 10 and the cervical spine A becomes long. Therefore, since the X-ray cone beam B from the X-ray generating section 10 reaches the cervical spine A in an expanded state, part of the X-ray cone beam B intersects with the cervical spine A as shown in FIG. 22(g), thereby to have a small influence on the imaging result of the cervical spine A as compared with the case of FIG. 21(c). Accordingly, in the X-ray output profile, the X-ray output in the case of FIG. 22(g) is small as compared with that in the case of FIG. 21(c).

Further described is an influence on the X-ray output profile in the case of a cervical spine of a patient I shown in FIG. 23(a) and a cervical spine of a patient II shown in FIG. 23(b) being located in different places. As shown in FIG. 23(b), a cervical spine AII of the patient II is located closer to the dental arch r side as compared with a cervical spine AI of the patient I. Therefore, as shown in FIG. 23(c), a line connecting between the X-ray generating section 10 and the X-ray image capturing section 20 intersects with the cervical spine AI in a position where the rotational arm rotates around the central coordinate (Xa, Ya) with an angle of θI. On the other hand, as shown in FIG. 23(d), the line connecting between the X-ray generating section 10 and the X-ray image capturing section 20 intersects with the cervical spine AII in a position where the rotational arm rotates around the central coordinate (Xa, Ya) with an angle of θII (<θI).

Namely, when the cervical spine is located closer to the dental arch r side, the line connecting the X-ray generating section 10 and the X-ray image capturing section 20 intersects with the cervical spine in an earlier stage (with an smaller rotational angle). Therefore, the X-ray output profile becomes as in FIG. 23(e), and the X-ray output reaches its peak in the X-ray output profile for the patient II in an earlier stage than in the X-ray output profile for the patient I.

It is to be noted that as shown in FIG. 23(f), an X-ray output profile positioned between the X-ray output profile for the patient I and the X-ray output profile for the patient II may be adopted as a control model for use in the X-ray CT imaging apparatus M.

As thus described, in the X-ray CT imaging apparatus M according to the present embodiment, only a local portion of the object o is made an object to be imaged, whereby it is possible to apply the apparatus to a variety of X-ray CT imaging apparatuses and also reduce an X-ray dose given to an object (patient).

While the invention has been shown and described in detail, the foregoing description is in all aspects illustrative and not restrictive. It is therefore understood that numerous modifications and variations can be devised without departing from the scope of the invention.

What is claimed is:

1. An X-ray CT imaging apparatus comprising:
    an X-ray generating section for generating an X-ray cone beam;
    an X-ray image capturing section for detecting said X-ray cone beam generated from said X-ray generating section, having passed through an object;
    a supporting section for supporting said X-ray generating section and said X-ray image capturing section with said object positioned therebetween;
    a holding section for holding said object;
    a rotation driving section for rotating said supporting section relatively to said object; and
    an X-ray controlling section for alleviating an influence of a high X-ray absorption region, existing outside of the CT imaging area, present inside said object, in imaging by said X-ray image capturing section, by increasing the output of said X-ray cone beam while said supporting section is within a rotational angle where said X-ray cone beam passes through both of said CT imaging area and said high X-ray absorption region by a larger amount of said X-ray cone beam than while said supporting section is within a rotational angle where said X-ray cone beam passes through said CT imaging area but does not pass through said high X-ray absorption region by means of a previously arranged control model formed based upon high X-ray absorption region information as information on a position of the high X-ray absorption region.

2. The X-ray CT imaging apparatus according to claim 1, wherein said apparatus further comprises a region information acquiring section for acquiring said high X-ray absorption region information, and
    said X-ray controlling section alleviates the influence of said high X-ray absorption region in imaging by said X-ray image capturing section by means of said control model formed based upon said high X-ray absorption region information acquired in said region information acquiring section.

3. The X-ray CT imaging apparatus according to claim 2, wherein said region information acquiring section acquires said high X-ray absorption region information from a scout image obtained by scout-imaging of said object before X-ray CT imaging.

4. The X-ray CT imaging apparatus according to claim 3, wherein said scout image is at least one of an image obtained by imaging said object from two different directions and a curved surface tomographic image of said object.

5. The X-ray CT imaging apparatus according to claim 3, wherein said scout image is an image read from a storage section inside said X-ray CT imaging apparatus or an external storage section, associated hereto.

6. The X-ray CT imaging apparatus according to claim 3, wherein said region information acquiring section specifies said high X-ray absorption region from said scout image by image pattern recognition.

7. The X-ray CT imaging apparatus according to claim 2, wherein said region information acquiring section selects a body type of said object from predetermined alternatives, to acquire said high X-ray absorption region information previously set in accordance with said predetermined alternative.

8. The X-ray CT imaging apparatus according to claim 2, wherein said region information acquiring section specifies the high X-ray absorption region based upon measurement data of said object.

9. The X-ray CT imaging apparatus according to claim 8, wherein measurement of said object is performed by use of said holding section.

10. The X-ray CT imaging apparatus according to claim 1, wherein
    said apparatus further comprises an X-ray transmission amount monitoring section for monitoring an amount of transmitted X-rays in a place constantly irradiated with said X-ray cone beam, and
    said X-ray transmission amount monitoring section corrects said control model of said X-ray controlling section so as to make said monitored amount of transmitted X-rays a substantially constant value.

11. The X-ray CT imaging apparatus according to claim 1, wherein said X-ray controlling section controls at least one of an output of said X-ray cone beam and a relative rotational speed of said supporting section by means of said control model in accordance with a rotational angle of said supporting section.

12. The X-ray CT imaging apparatus according to claim 11, wherein said X-ray controlling section changes at least one of a tube current and a tube voltage of said X-ray generating section, to control the output of said X-ray cone beam.

13. The X-ray CT imaging apparatus according to claim 1, wherein said X-ray controlling section changes a rotational speed of at least one of said supporting section and said object by said rotation driving section, to control the relative rotational speed of said supporting section.

14. The X-ray CT imaging apparatus according to claim 1, wherein said high X-ray absorption region is a cervical spine.

15. The X-ray CT imaging apparatus according to claim 1, wherein the object to be imaged of said X-ray CT imaging apparatus is only a local portion of said object.

16. The X-ray CT imaging apparatus according to claim 15, wherein each of control models that are different is set with respect to each local portions of said object.

17. An X-ray CT imaging apparatus comprising:
- an X-ray generating section for generating an X-ray cone beam;
- an X-ray image capturing section for detecting said X-ray cone beam generated from said X-ray generating section, having passed through an object;
- a supporting section for supporting said X-ray generating section and said
- X-ray image capturing section with said object positioned therebetween;
- a holding section for holding said object;
- a rotation driving section for rotating said supporting section relatively to said object and
- an X-ray controlling section for alleviating an influence of a high X-ray absorption region, existing outside of the CT imaging area, present inside said object, in imaging by said X-ray image capturing section, by increasing the output of said X-ray cone beam while said supporting section is within a rotational angle where said X-ray cone beam passes through both of said CT imaging area and said high X-ray absorption region by a larger amount of said X-ray cone beam than while said supporting section is within a rotational angle where said X-ray cone beam passes through said CT imaging area but does not pass through said high X-ray absorption region by means of a previously arranged control model formed based upon high X-ray absorption region information as information on a position of the high X-ray absorption region;
- wherein said apparatus further comprises:
- a central axis setting section for setting a position of a rotation central axis of said X-ray generating section and said X-ray image capturing section; and
- a rotation central axis shifting section for shifting the position of said rotation central axis relatively to said object in a two-dimensional direction crossing a direction of said rotation central axis based upon the setting in said central axis setting section, and
- said X-ray controlling section alleviates the influence of said high X-ray absorption region in imaging by said X-ray image capturing section by means of said control model formed in consideration of the position of said rotation central axis.

18. An imaging controlling method for an X-ray CT imaging apparatus, comprising the steps of
- (a) holding an object in an holding section;
- (b) making an X-ray image capturing section detect an X-ray cone beam from an X-ray generating section, having passed through the object, while rotating a supporting section for supporting said X-ray generating section and said X-ray image capturing section relatively to said object; and
- (c) making an X-ray controlling section alleviate an influence of a high X-ray absorption region, existing outside of the CT imaging area, present inside said object held in said step (a), in imaging by said X-ray image capturing section during processing of said step (b), increasing the output of said X-ray cone beam while said supporting section is within a rotational angle where said X-ray cone beam passes through both of said CT imaging area and said high X-ray, absorption region by a larger amount of said X-ray cone beam than while said supporting section is within a rotational angle where said X-ray cone beam passes through said CT imaging area but does not pass through said high X-ray absorption region by means of a previously arranged control model formed based upon high X-ray absorption region information as information concerning a position of said high X-ray absorption region.

19. The imaging controlling method for an X-ray CT imaging apparatus, according to claim 18,
wherein said method further comprises the steps of:
- (d) acquiring said high X-ray absorption region information by use of a region information acquiring section; and
- (e) selecting the control model formed based upon said high X-ray absorption region information acquired in said step (d), to make said X-ray controlling section alleviate the influence of said high X-ray absorption region in imaging by said X-ray image capturing section.

20. The imaging controlling method for an X-ray CT imaging apparatus according to claim 18, wherein said X-ray controlling section controls at least one of an output of said X-ray cone beam and a relative rotational speed of said supporting section during processing of said step (b) by means of said control model, to alleviate the influence of said high X-ray absorption region in imaging by said X-ray image capturing section.

21. An imaging controlling method for an X-ray CT imaging apparatus, comprising the steps of:
- (a) holding an object in an holding section;
- (b) making an X-ray image capturing section detect an X-ray cone beam from an X-ray generating section, having passed through the object, while rotating a supporting section for supporting said X-ray generating section and said X-ray image capturing section relatively to said object: and
- (c) making an X-ray controlling section alleviate an influence of a high X-ray absorption region, existing outside of the CT imaging area, present inside said object held in said step (a), in imaging by said X-ray image capturing section during processing of said step (b), increasing the output of said X-ray cone beam while said supporting section is within a rotational angle where said X-ray cone beam passes through both of said CT imaging area and said high X-ray absorption region by a larger amount of said X-ray cone beam than while said supporting section is within a rotational angle where said X-ray cone beam passes through said CT imaging area but does not pass through said high X-ray absorption region by means of a previously arranged control model formed based upon high X-ray absorption region information as information concerning a position of said high X-ray absorption region, wherein
said method further comprises the steps of
- (d) acquiring said high X-ray absorption region information by use of a region information acquiring section;

(e) selecting the control model formed based upon said high X-ray absorption region information acquired in said step (d), to make said X-ray controlling section alleviate the influence of said high X-ray absorption region in imaging by said X-ray image capturing section, (f) setting a position of a rotation central axis of said X-ray generating section and said X-ray image capturing section by use of a central axis setting section after said step (a); and (g) making a rotation central axis shifting section shift the position of said rotation central axis relatively to said object in two-dimensional directions crossing a direction of said rotation central axis, based upon the setting in said step (f), and said X-ray controlling section alleviates the influence of said high X-ray absorption region in imaging by said X-ray image capturing section by means of said control model formed in consideration of the position of said rotation central axis in the setting of said step (f).

* * * * *